US011896670B2

(12) United States Patent
Trachsel et al.

(10) Patent No.: US 11,896,670 B2
(45) Date of Patent: Feb. 13, 2024

(54) SYNTHESIS ROUTES TO ACCESS MDMA PRODRUGS BY USING CONTROLLED AND NON-CONTROLLED INTERMEDIATES

(71) Applicant: Mind Medicine, Inc., New York, NY (US)

(72) Inventors: Daniel Trachsel, Detligen (CH); Matthias Emanuel Liechti, Oberwil (CH); Felix Lustenberger, Meggen (CH)

(73) Assignee: Mind Medicine, Inc., New York, NY (US)

( * ) Notice: Subject to any disclaimer, the term of this patent is extended or adjusted under 35 U.S.C. 154(b) by 0 days.

(21) Appl. No.: 17/893,292

(22) Filed: Aug. 23, 2022

(65) Prior Publication Data

US 2023/0066171 A1 Mar. 2, 2023

Related U.S. Application Data

(60) Provisional application No. 63/236,498, filed on Aug. 24, 2021.

(51) Int. Cl.
*A61K 47/54* (2017.01)

(52) U.S. Cl.
CPC .......... *A61K 47/542* (2017.08); *A61K 47/545* (2017.08)

(58) Field of Classification Search
CPC ................................................... A61K 47/545
See application file for complete search history.

(56) References Cited

U.S. PATENT DOCUMENTS

2009/0131516 A1* 5/2009 Mickle ............... A61P 25/34
514/626

FOREIGN PATENT DOCUMENTS

JP 31008779 * 10/1956

OTHER PUBLICATIONS

Sitte, Trends Pharmacol Sci. 2015; 36(1): 41-50, 2014.*
Guy, Cent. Eur. J. Chem. • 6(4) • 2008 • 526-534.*
Kadkhodaei, Journal of Separation Science (2018), 41(6), 1274-1286 M.*
Mattha Busby, The intercept, Jul. 26, 2022.*
Takagi, Chemical & Pharmaceutical Bulletin (1963), 11(5), 654-7.*
Baggott MJ, Garrison KJ, Coyle JR, Galloway GP, Barnes AJ, Huestis MA, & Mendelson JE (2019). Effects of the Psychedelic Amphetamine MDA (3,4-Methylenedioxyamphetamine) in Healthy Volunteers. J Psychoactive Drugs 51: 108-117.
Calderon SN, Hunt J, & Klein M (2018). A regulatory perspective on the evaluation of hallucinogen drugs for human use. Neuropharmacology 142: 135-142.
Carhart-Harris RL, & Goodwin GM (2017). The therapeutic potential of psychedelic drugs: past, present, and future. Neuropsychopharmacology 42: 2105-2113.
Danforth A Exploring MDMA-assisted therapy as a new pathway to social adaptabilty for autistic adults.
Danforth AL, Grob CS, Struble C, Feduccia AA, Walker N, Jerome L, Yazar-Klosinski B, & Emerson A (2018). Reduction in social anxiety after MDMA-assisted psychotherapy with autistic adults: a randomized, double-blind, placebo-controlled pilot study. Psychopharmacology (Berl) 235: 3137-3148.
Danforth AL, Struble CM, Yazar-Klosinski B, & Grob CS (2016). MDMA-assisted therapy: a new treatment model for social anxiety in autistic adults. Prog Neuropsychopharmacol Biol Psychiatry 64: 237-249.
Holze F, Vizeli P, Muller F, Ley L, Duerig R, Varghese N, Eckert A, Borgwardt S, & Liechti ME (2020). Distinct acute effects of LSD, MDMA, and D-amphetamine in healthy subjects. Neuropsychopharmacology 45: 462-471.
Hysek CM, Schmid Y, Simmler LD, Domes G, Heinrichs M, Eisenegger C, Preller KH, Quednow BB, & Liechti ME (2014). MDMA enhances emotional empathy and prosocial behavior. Soc Cogn Affect Neurosci 9: 1645-1652.
Liechti ME (2017). Modern clinical research on LSD. Neuropsychopharmacology 42: 2114-2127.
Luethi D, Kolaczynska KE, Walter M, Suzuki M, Rice KC, Blough BE, Hoener MC, Baumann MH, & Liechti ME (2019). Metabolites of the ring-substituted stimulants MDMA, methylone and MDPV differentially affect human monoaminergic systems. J Psychopharmacol 33: 831-841.
Luoma JB, Chwyl C, Bathje GJ, Davis AK, & Lancelotta R (2020). A Meta-Analysis of Placebo-Controlled Trials of Psychedelic-Assisted Therapy. J Psychoactive Drugs: 1-11.
Mithoefer MC, Feduccia AA, Jerome L, Mithoefer A, Wagner M, Walsh Z, Hamilton S, Yazar-Klosinski B, Emerson A, & Doblin R (2019). MDMA-assisted psychotherapy for treatment of PTSD: study design and rationale for phase 3 trials based on pooled analysis of six phase 2 randomized controlled trials. Psychopharmacology (Berl).
Mithoefer MC, Wagner MT, Mithoefer AT, Jerome I, & Doblin R (2010). The safety and efficacy of ±3,4-methylenedioxymethamphetamine-assisted psychotherapy in subjects with chronic, treatment-resistant posttraumatic stress disorder: the first randomized controlled pilot study. J Psychopharmacol 25: 439-452.
Nichols DE, Johnson MW, & Nichols CD (2017). Psychedelics as medicines: an emerging new paradigm. Clin Pharmacol Ther 101: 209-219.
Oehen P, Traber R, Widmer V, & Schnyder U (2013). A randomized, controlled pilot study of MDMA (±3,4-methylenedioxymethamphetamine)-assisted psychotherapy for treatment of resistant, chronic post-traumatic stress disorder (PTSD). J Psychopharmacol 27: 40-52.
Oeri HE (2020). Beyond ecstasy: Alternative entactogens to 3,4-methylenedioxymethamphetamine with potential applications in psychotherapy. J Psychopharmacol: 269881120920420.

(Continued)

*Primary Examiner* — Nizal S Chandrakumar
(74) *Attorney, Agent, or Firm* — Kohn & Associates PLLC; Kenneth I. Kohn; Laura S. Dellal (57) ABSTRACT

A method of synthesizing a pharmacological compound substance by attaching a psychoactive base substance to an amino acid and creating a prodrug with modified pharmacological behavior. A prodrug made by the method. A pharmaceutical composition comprising a prodrug of a psychoactive base substance attached to an amino acid and a pharmaceutically acceptable salt.

2 Claims, 6 Drawing Sheets

(56) References Cited

OTHER PUBLICATIONS

Pentney AR (2001). An exploration of the history and controversies surrounding MDMA and MDA. J Psychoactive Drugs 33: 213-221.
Rickli A, Hoener MC, & Liechti ME (2015a). Monoamine transporter and receptor interaction profiles of novel psychoactive substances: para-halogenated amphetamines and pyrovalerone cathinones. Eur Neuropsychopharmacol 25: 365-376.
Rickli A, Kopf S, Hoener MC, & Liechti ME (2015b). Pharmacological profile of novel psychoactive benzofurans. Br J Pharmacol 172: 3412-3425.
Sessa B, Higbed L, & Nutt D (2019). A Review of 3,4-methylenedioxymethamphetamine (MDMA)-Assisted Psychotherapy. Front Psychiatry 10: 138.
Simmler L, Buser T, Donzelli M, Schramm Y, Dieu LH, Huwyler J, Chaboz S, Hoener M, & Liechti ME (2013). Pharmacological characterization of designer cathinones in vitro. Br J Pharmacol 168: 458-470.
Trope A, Anderson BT, Hooker AR, Glick G, Stauffer C, & Woolley JD (2019). Psychedelic-Assisted Group Therapy: a Systematic Review. J Psychoactive Drugs 51: 174-188.
Yensen R, Di Leo FB, Rhead JC, Richards WA, Soskin RA, Turek B, & Kurland AA (1976). MDA-assisted psychotherapy with neurotic outpatients: a pilot study. J Nerv Ment Dis 163: 233-245.

\* cited by examiner

Fig. 1

LysMDMA

MDA

Fig. 2A

MDMA

Fig. 2B

MDEA

Fig. 2C

BDB

Fig. 2D

MBDB

Fig. 2E methylone

Fig. 2F ethylone

Fig. 2G

MDAI

Fig. 2H

5-IAI

Fig. 2I

4-APB

Fig. 2J

5-APB

Fig. 2K

6-APB

Fig. 2L

5-MAPDB

Fig. 2M

5-MAPB

Fig. 2N

6F-MDA

Fig. 2O

5F-MDA

Fig. 2P

2F-MDA

Fig. 2Q

7; L-Lys-(R,S)-MDA

Fig. 3A

9; L-Lys-(R,S)-MDMA

Fig. 3B

20; D-Lys-(R,S)-MDMA

SYNTHESIS ROUTES TO ACCESS MDMA PRODRUGS BY USING CONTROLLED AND NON-CONTROLLED INTERMEDIATES

BACKGROUND OF THE INVENTION

1. Technical Field

The present invention relates a method to synthetically access to MDMA and MDMA-like prodrugs by using controlled precursors and a further synthetic route by omitting such controlled precursors to gain access to compounds to be used in substance-assisted psychotherapy.

2. Background Art 3,4-Methylenedioxymethamphetamine (MDMA) is a psychoactive drug that alters mood and perception, and is investigated as an adjunct in psychotherapy for posttraumatic stress disorder (PTSD), social anxiety, autism (Danforth, 2016; Danforth et al., 2018; Danforth et al., 2016; Mitchell et al., 2021; Mithoefer et al., 2019; Mithoefer et al., 2010; Oehen et al., 2013), and is being studied and used for a range of other medical conditions. Such conditions where MDMA or related substances can be useful include, but is not limited to, substance-use disorder, depression, anxiety disorder, anxiety with life-threatening disease, personality disorder including narcissistic and antisocial disorder, and obsessive-compulsive disorder. MDMA or related substances may also be used to enhance couple therapy. Substances related to MDMA can be chemically similar and/or pharmacologically similar and produce psychoactive effects that are like those of MDMA.

MDMA and pharmacologically related substances are thought to produce positive therapeutic long-term effects in the context of MDMA/substance-assisted psychotherapy by producing acute subjective positive mood effects that also enhance the effectiveness of psychotherapy and can be beneficial on their own. Such acute beneficial MDMA-effects include, but are not limited to, feelings of well-being, feelings of connectivity to others, feelings of increased trust, feelings of love, enhanced emotional empathy, and enhanced feelings of pro-sociality and prosocial behavior (Hysek et al., 2014).

Previously, substances including MDMA, psilocybin, and lysergic acid diethylamide (LSD) have been used in substance-assisted psychotherapy (Carhart-Harris & Goodwin, 2017; Liechti, 2017; Luoma et al., 2020; Nichols et al., 2017; Sessa et al., 2019; Trope et al., 2019). However, other MDMA-like substances can be more suitable with different therapeutic benefits/tolerability profiles. Additionally, MDMA is the only empathogen-type substance currently investigated for substance-assisted psychotherapy while psilocybin and LSD are psychedelics with a different effect profile and mode of action (Holze et al., 2020). Alternatives to MDMA have been suggested (Oeri, 2020). These alternative MDMA-like substances include many compounds that can share some similarity with MDMA based on their in vitro pharmacological profiles and based on reports of their subjective effects by recreational users (Oeri, 2020). Thus, "MDMA-like" refers to both a similar pharmacological profile to MDMA and/or a prodrug of MDMA or a related psychoactive substance and/or similar empathogenic/entactogenic subjective effects compared to MDMA.

3,4-Methylenedioxamphetamine (MDA) is pharmacologically relatively like MDMA and at the same time the only MDMA-like substance which has been used to assist psychotherapy in the past (Baggott et al., 2019; Yensen et al., 1976).

U.S. provisional patent application No. 63/115,245 discloses optimized effects of MDMA and MDA by using a pro-drug approach. This allowed modification of the MDMA and MDA effects but at the same time the novel compounds are transformed to the known and previously used active substances MDMA and MDA in the body potentially providing higher safety compared to a compound with a novel structure of the active entity. MDMA may not be the only compound suitable for substance-assisted therapy. In fact, MDMA can be contraindicated in some subjects (for example due to cardiovascular side effects) and substance characteristics slightly different from those of MDMA may be needed in some patients.

Therefore, substances with expected overall similar benefits as those of MDMA in MDMA-assisted therapy are needed, while such substances could be improved regarding some of the adverse effects of MDMA or could exhibit properties in addition to MDMA that are of therapeutic interest.

SUMMARY OF THE INVENTION

The present invention provides for a method of synthesizing a pharmacological compound substance by attaching a psychoactive base substance to an amino acid and creating a prodrug with modified pharmacological behavior.

The present invention provides for a prodrug made by the above method.

The present invention provides for a pharmaceutical composition comprising a prodrug of a psychoactive base substance attached to an amino acid and a pharmaceutically acceptable salt.

DESCRIPTION OF THE DRAWINGS

Other advantages of the present invention are readily appreciated as the same becomes better understood by reference to the following detailed description when considered in connection with the accompanying drawings wherein:

FIGS. 2A-2Q show, as illustrative examples, MDMA and MDMA-like drugs to be used for prodrugs represented by FIG. 1, FIG. 2A is MDA, FIG. 2Q is 2F-MDA;

DETAILED DESCRIPTION OF THE INVENTION

The present invention provides for methods of synthesizing compounds including an amino acid covalently attached/bonded to a psychoactive base substance from the group of empathogens, entactogens or MDMA-like substances such as MDMA or an MDMA-like compound with psychoactive action (FIGS. 1-3C). These MDMA-like compounds and/or prodrugs of MDMA or MDMA-like substances can substitute for MDMA in selected patients. The possible advantages of these MDMA-like substances, including prodrugs of MDMA, MDA, MDEA, etc. and the type of compounds to substitute for MDMA have been reported in the U.S. provisional patent application No. 63/115,245, filed previously. The present invention provides synthesis methods for MDMA prodrugs and MDMA-like prodrugs from non-controlled precursors without producing scheduled substances in the process of synthesis. The present invention also provides for a compound of a prodrug including a psychoactive base substance attached to an amino acid.

A "prodrug" as used herein, refers to a compound that includes a moiety attached to an active drug substance that is metabolized after administration to an individual and the compound is converted into the active drug substance. Using a prodrug allows for improving how the active drug is absorbed, distributed, metabolized, and excreted.

Prodrugs can be used to be absorbed more completely compared with the administration of the parent drugs and to release the parent drug not in the intestine but only when reaching the circulation and at a favorable releasing rate. Prodrugs can also be used to lower the extent of release to keep plasma levels lower. An extended or lowered rate of release can also happen in the gastrointestinal tract.

The MDMA and/or MDMA-like compound is coupled with any natural or unnatural amino acid to form an amide bound that is broken by a human's body to liberate the MDMA-like compound. The amino acid can be lysine or any other amino acid such as alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine and typically attached to the amine (N)-group of MDMA or the MDMA-like substance and hence reducing or even completely avoiding pharmacological activity at the primary site of action (cell-membrane monoamine transporters including serotonin, dopamine and norepinephrine transporter) compared with the psychoactive substance, and altering extent and rate of absorption and mainly releasing active substance in the circulation after absorption of the inactive compound. The amino acid can preferably be lysine or any other amino acid with the natural L configuration as well as with the D configuration and in any L-to-D ratio. Also provided is an example synthesis using lysine as the amino acid combined with MDMA and MDA. However, the invention is not limited to lysine as amino acid and can use any other natural or unnatural amino acid covalently bound to any other MDMA-like substance via the amine group of the MDMA-like substance to form a peptide bond.

The MDMA-like compound can be MDMA (FIG. 2B), MDA (FIG. 2A), 3,4-methylenedioxyethylamphetamine (MDEA) (FIG. 2C), 1-(1,3-benzodioxol-5-yl)methyl butanamine (MBDB) (FIG. 2E), 1-(1,3-benzodioxol-5-yl)-2-aminobutane (BDB, also known as MDB) (FIG. 2D), methylone (FIG. 2F), ethylone (FIG. 2G), 5,6-methylenedioxy aminoindane (MDAI) (FIG. 2H), 5-iodo-2-aminoindane (5-IAI) (FIG. 2I), 4-(2-aminopropyl)-benzofuran (4-APB) (FIG. 2J), 5-(2-aminopropyl)-benzofuran (5-APB) (FIG. 2K), 6-(2-aminopropyl)-benzofuran (6-APB) (FIG. 2L), 1-(2,3-dihydrobenzofuran-5-yl)-N-methylpropan-2-amine (5-MAPDB) (FIG. 2M), 5-(2-methylaminopropyl)-benzofuran (5-MAPB) (FIG. 2N), 2F-MDA (FIG. 2Q), 5F-MDA (FIG. 2P), 6F-MDA (FIG. 2O), or other compounds, namely a benzofuran, aminoindane or cathinone or mixed dopaminergic-serotonergic amphetamines and their N-alkylated analogs, with an MDMA-like pharmacological profile (Rickli et al., 2015a; Rickli et al., 2015b; Simmler et al., 2013) or active metabolites of such substances (Luethi et al., 2019), etc. The compounds of invention are basic compounds which form acid addition salts with inorganic or organic acids. Therefore, they form pharmaceutically acceptable inorganic and organic salts with pharmacologically acceptable inorganic or organic acids. Acids to form such salts can be selected from inorganic acids such as hydrochloric acid, hydrobromic acid, hydroiodic acid, sulfuric acid, nitric acid, phosphoric acid, and the like, and organic acids, such as carbonic acid, p-toluenesulfonic acid, methanesulfonic acid, oxalic acid, succinic acid, citric acid, benzoic acid, and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyro-phosphate, chloride, bromide, iodide, formate, acetate, propionate, decanoate, caprylate, acrylate, isobutyrate, caproate, heptanoate, oxalate, malonate, succinate, suberate, sebacate, fumarate, maleate, benzoate, phthalate, sulfonate, phenylacetate, citrate, lactate, glycollate, tartrate, methanesulfonate, propanesulfonate, mandelate and the like. Any hydrated form and any ratio of compound of invention to pharmacologically acceptable inorganic or organic acids can be formed. Where applicable, within the salt forming acid, any stereochemical configuration is included. Preferred pharmaceutically acceptable salts are those formed with hydrochloric acid and methanesulfonic acid.

Any of the pharmaceutically acceptable salts can also contain one or more deuteron or fluorine atoms and any stereoisomers are included.

Figure 1:
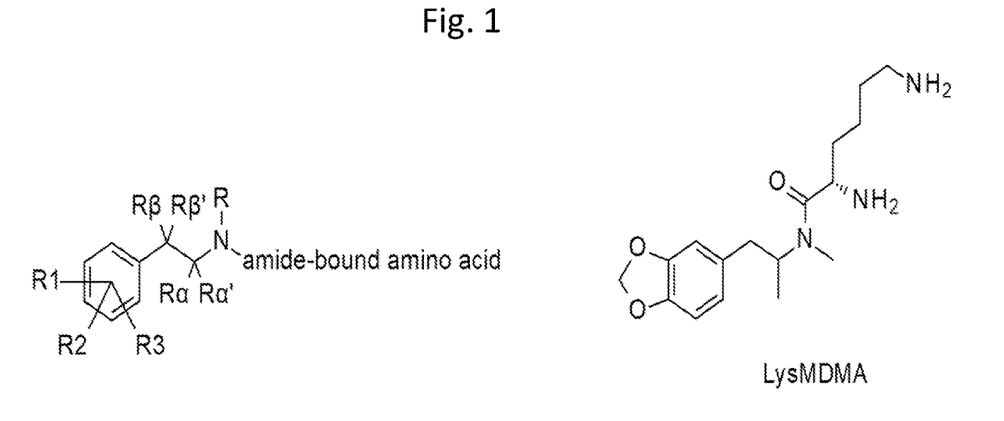
FIG. 1 shows the chemical structure of MDMA and MDMA-like prodrugs and also shows, as a representative example, the prodrug lysMDMA as a part of the invention.
Figure 2A:
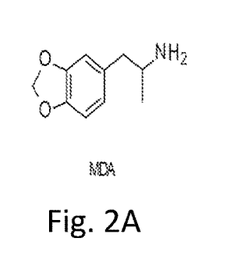
Figure 2B:
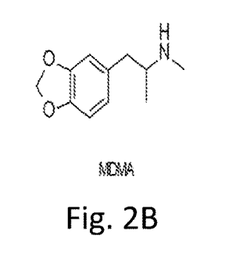
FIG. 2B is MDMA.
Figure 2C:
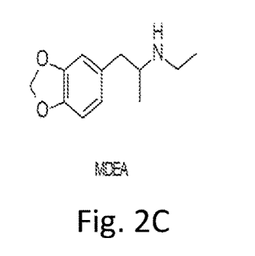
FIG. 2C is MDEA.
Figure 2D:
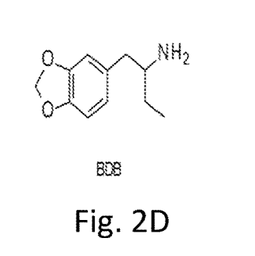
FIG. 2D is BDB.
Figure 2E:
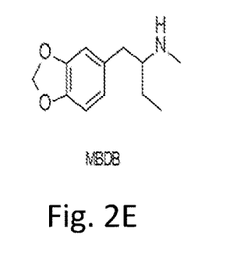
FIG. 2E is MBDB.
Figure 2F:
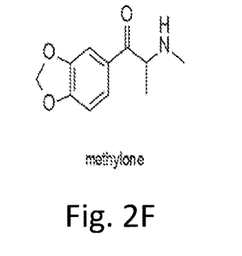
FIG. 2F is methylone.
Figure 2G:
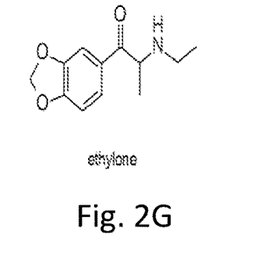
FIG. 2G is ethylone.
Figure 2H:
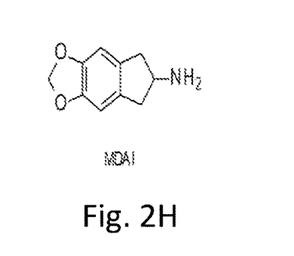
FIG. 2H is MDAI.
Figure 2I:
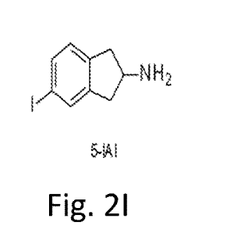
FIG. 2I is 5-IAI.
Figure 2J:
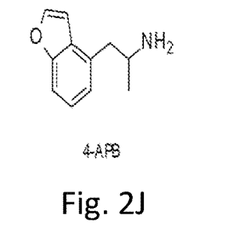
FIG. 2J is 4-APB.
Figure 2K:
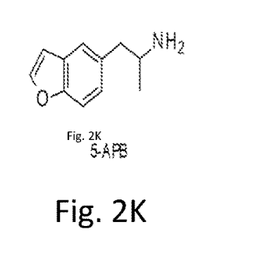
FIG. 2K is 5-APB.
Figure 2L:
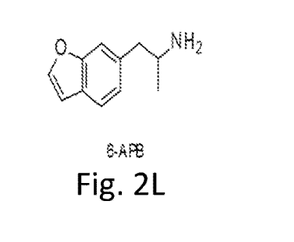
FIG. 2L is 6-APB.
Figure 2M:
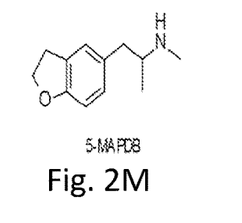
FIG. 2M is 5-MAPDB.
Figure 2N:
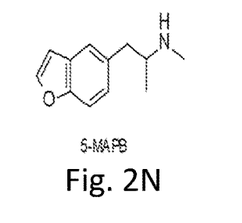
FIG. 2N is 5-MAPB.
Figure 2O:
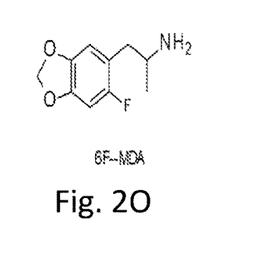
FIG. 2O is 6F-MDA.
Figure 2P:
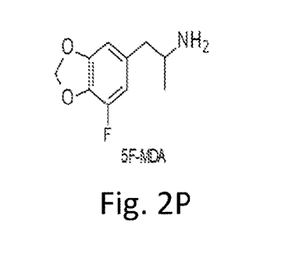
FIG. 2P is 5F-MDA.
Figure 2Q:
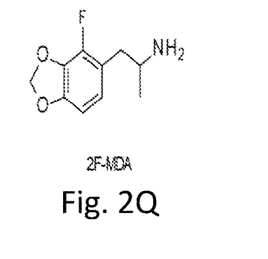
Figure 3A:
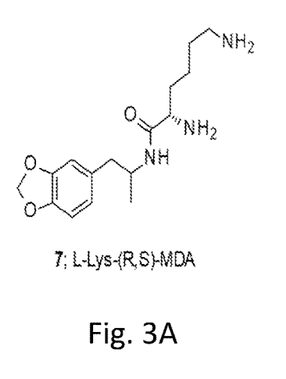
FIGS. 3A-3C show illustrative examples (compounds 7 (FIG. 3A), 9 (FIG. 3B), and 20 (FIG. 3C)) of MDMA- and MDMA-like prodrugs represented by FIG. 1.
Figure 3B:
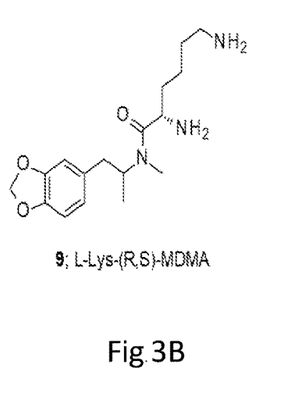
Figure 3C:
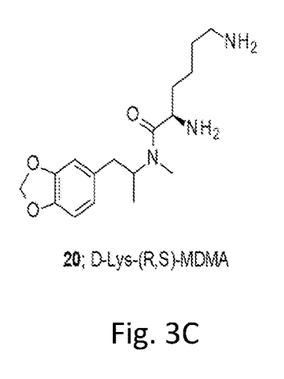

FIG. 1 shows the chemical structure of the MDMA and MDMA-like prodrugs with MDMA-like psychoactive action, where R is 1.) hydrogen, branched or unbranched alkyl such as methyl, ethyl, propyl, isopropyl, 2.) cycloalkyl such as cyclopropyl or cyclobutyl, 3.) cycloalkylalkyl such as cyclopropylmethyl or cyclobutylethyl, or 4.) any of the aforementioned substituents containing one or more additional fluorine, deuterium, alkyl, double bond or triple bond; Ra and Ra' are, in any combination and independently, 1.) hydrogen, branched or unbranched alkyl such as methyl, ethyl, propyl, isopropyl, 2.) cycloalkyl such as cyclopropyl or cyclobutyl, 3.) cycloalkylalkyl such as cyclopropylmethyl or cyclobutylethyl, or 4.) any of the aforementioned substituents containing one or more additional fluorine, deuterium, alkyl, double bond or triple bond, 5.) a deuterium or fluorine; Ra and Ra' are connected together to form 1.) any cycloalkyl such as cyclopropyl or cyclobutyl with none, one or more deuterium, fluorine or alkyl or any other heteroatom substituent attached to it, 2.) any oxa-, aza- or thiacycloalkyl with none, one or more additional fluorine, deuterium, alkyl, double bond or triple bond or any other heteroatom substituent attached to it; Ra and/or Ra' is 1.) any alkyl, alkenyl or alkynyl connected to the aryl moiety to form a benzannelated ring with bearing none, one or more additional fluorine, deuterium, double bond, alkyl, alkenyl or alkylidene or any heteroatom substituent; Rβ and Rβ' are, in any combination and independently, 1.) hydrogen, branched or unbranched alkyl such as methyl, ethyl, propyl, isopropyl, 2.) cycloalkyl such as cyclopropyl or cyclobutyl, 3.) cycloalkylalkyl such as cyclopropylmethyl or cyclobutylethyl, or 4.) any of the aforementioned substituents containing one or more additional fluorine, deuterium, alkyl, double bond or triple bond, 5.) a deuterium or fluorine; Rβ and Rβ' are connected together to form 1.) any cycloalkyl such as cyclopropyl or cyclobutyl with none, one or more deuterium, fluorine or alkyl or any other heteroatom substituent attached to it, 2.) any oxa-, aza- or thiacycloalkyl with none, one or more deuterium, fluorine or alkyl or any other heteroatom substituent attached to it, 3.) an oxo or thio substituent, 4.) any alkylidene substituent such as methylidene, ethylidene or propylidene with none, one or more deuterium, fluorine, alkyl or cycloalkyl substituents; Rβ and/or Rβ' is 1.) any alkyl, alkenyl or alkynyl connected to the aryl moiety to form a benzannelated ring with bearing none, one or more additional fluorine, deuterium, double bond, alkyl, alkenyl or alkylidene or any heteroatom substituent; R1, R2 and R3 are, in any combination and independently, 1.) hydrogen, branched or unbranched alkyl such as methyl, ethyl, propyl, isopropyl, 2.) cycloalkyl such as cyclopropyl or cyclobutyl, 3.) cycloalkylalkyl such as cyclopropylmethyl or cyclobutylethyl, 4.) unbranched or branched ether or thioether such as methoxy, ethoxy or methylthio, ethylthio, isopropylthio, 5.) an halogen such as fluorine, chlorine, bromine or iodine, 6.) any of the aforementioned substituents containing one or more additional fluorine, deuterium, alkyl, double bond or triple bond; at least two of the substituents R1, R2 and R3 are connected together to form benzannelated 1.) cycloalkanes, oxacycloalkanes, thiacycloalkanes, dioxacycloalkanes, oxathiacycloalkanes or azacycloalkanes all containing none, one or more additional double bonds, deuterium, fluorine or any other heteroatom, alkyl or alkenyl or alkylidene substituents. In addition, for FIG. 1, where applicable, E and Z or cis and trans configurations for any double bond containing compound are included. Also, where applicable, the stereocenters can be any possible configuration and are not limited in any way. Thus, any enantiomeric or diastereomeric ratios possible are included. The term "amide-bound amino acid" in FIG. 1 refers to any natural (L configuration) or unnatural (D configuration) amino acid whereas the carboxyl part of the amino acid is chemically bound to the basic nitrogen of the MDMA or MDMA-like compound. The present invention provides for any of the compounds described above.

Psychoactive base substances to be used in the present invention include or MDMA-like substance such as, but not limited to, MDMA, MDA, MDEA, MBDB, BDB, MDB, 2F-MDA, 5F-MDA, 6F-MDA, ethylone, MDAI, 5-IAI, 4-APB, 5-APB, 6-APB, 5-MAPDB, 5-MAPB, and/or mixed dopaminergic-serotonergic amphetamines and their N-alkylated analogs, and/or active metabolites of such substances.

The compounds represented by FIG. 1 are basic compounds which form acid addition salts with inorganic or organic acids. Therefore, they form pharmaceutically acceptable inorganic and organic salts with pharmacologically acceptable inorganic or organic acids. Acids to form such salts can be selected from inorganic acids such as hydrochloric acid, hydrobromic acid, hydroiodic acid, sulfuric acid, nitric acid, phosphoric acid, and the like, and organic acids, such as carbonic acid, p-toluenesulfonic acid, methanesulfonic acid, oxalic acid, succinic acid, citric acid, benzoic acid, and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyro-phosphate, chloride, bromide, iodide, formate, acetate, propionate, decanoate, caprylate, acrylate, isobutyrate, caproate, heptanoate, oxalate, malonate, succinate, suberate, sebacate, fumarate, maleate, benzoate, phthalate, sulfonate, phenylacetate, citrate, lactate, glycollate, tartrate, methanesulfonate, propanesulfonate, mandelate and the like. Preferred pharmaceutically acceptable salts are those formed with hydrochloric acid.

The general chemical terms used for the FIG. 1 have their usual meanings. For example, the term "alkyl" includes such groups as methyl, ethyl, n-propyl, isopropyl, n-butyl, isobutyl, sec-butyl, tert-butyl, and the like. For another example, the term "cycloalkyl" includes such groups as cyclopropyl, cyclobutyl, cyclopentyl, and the like. Further on, the term "alkenyl" includes such groups as vinyl (ethenyl), 1-propenyl, 2-propenyl, isopropenyl, butenyl, and the like.

Those skilled in the art will appreciate that certain of the compounds of the present invention have at least one chiral carbon, and may therefore exist as a racemate, as individual enantiomers or diastereomers, and as mixtures of individual enantiomers or diastereomers in any ratio. For example, individual enantiomers of compounds of the invention are illustrated in FIG. 1 where Ra and Ra' as well as Rβ and Rβ' are Hydrogens. Those skilled in the art will further appreciate that those compounds of the invention where Rα≠Rα' or Rβ≠Rβ' in FIG. 1, the compound will bear an additional asymmetric center which create additional optical isomers as described above. While it is a preferred embodiment of the invention that the compounds of the invention are used as racemates or mixtures of diastereomers, the present invention also contemplates that the compounds of the invention existing in individual enantiomeric or diastereomeric pure form or in a mixture of any ratio.

The individual enantiomers and diastereomers can be prepared by chiral chromatography of the racemic or enantiomerically or diastereomerically enriched free amine, or fractional crystallization of salts prepared from racemic- or enantiomerically- or diastereomerically-enriched free amine and a chiral acid. Alternatively, the free amine can be reacted with a chiral auxiliary and the enantiomers or diastereomers separated by chromatography followed by removal of the chiral auxiliary to regenerate the free amine. Furthermore, separation of enantiomers or diastereomers can be performed at any convenient point in the synthesis of the compounds of the invention. The compounds of the invention can also be prepared by application of chiral syntheses. The compound itself is a pharmacologically acceptable acid addition salt thereof.

Throughout this invention, the term "Lys" or "lys" is representative for the natural amino-acid lysine in L configuration but is not limiting in any way to the use of the unnatural amino acid in D configuration.

Where detailed synthesis for illustrative examples of the field of inventions, represented by FIG. 1, are given, the configuration of the amino acid is indicated (e.g., D or L configuration). For the stereocenter-containing amines used as representative examples, no indication of the stereochemical configuration means the use of a racemate, e.g., "MDMA" means a 1:1 ratio of R-MDMA and S-MDMA.

Although stereochemical designations are not necessarily given throughout this invention, in no way is it limiting or excluding any possible configuration of a chiral center of any given intermediate or final prodrug described, be it generally or as representative example. That said, where no specification is given, this can address racemates or mixtures of stereoisomers, and contemplates the compounds of the invention existing in individual enantiomeric or diastereomeric pure form or in any ratio.

Compounds in the field of the present invention can be prepared in analogy to known routes such as described for lisdexamfetamine (patent numbers: WO2005032474A2, WO2006121552A2, U.S. Pat. No. 7,223,735B2, US2009234002A1, US20120157706A1, WO2017098533A2) which is derived from the combination of lysine as amino acid and dexamphetamine as psychoactive substance. Briefly, bis-N,N'-protected lysine or another correspondingly protected amino acid is activated at the carboxyl group by introducing a leaving group such as O-succinimide. In the present example, this activated lysine derivative is then allowed to react with a primary or secondary amine such as MDA or MDMA, respectively, to form the corresponding amide in the presence of a suitable non-protic base such as triethylamine, N-methylmorpholine or diisopropylethylamine. Tetrahydrofuran or dioxane is used as a suitable solvent, but others such as dimethylformamide, dimethylsulfoxide, or N-Methylpyrrolidone (NMP) can also be considered. After isolation and purification, the compounds such as bis-N,N'-protected lysMDA or lysMDMA are redissolved in a suitable solvent and treated with the corresponding conditions to allow deprotection, e.g., the use of an acid to remove tert-butoxycarbonyl groups, or hydrogen in the presence of a catalyst such as palladium on activated charcoal to remove hydrogen-sensitive protecting groups. The final products can either be isolated as a salt from corresponding conditions or as their free base. In an optional further purification step and/or conversion to a salt such as hydrochlorides or mesylates by known procedures lead to the final products such as lysMDA or lysMDMA or any similar combination of an MDMA-like psychoactive substance linked with an amino acid.

The present invention also describes the alternative synthesis of MDMA prodrugs and MDMA-like prodrugs using approaches that avoid the use of scheduled controlled substances like MDMA and MDA as in the example above. MDMA and related substances such as MDA are typically scheduled as narcotic in most if not all countries and producing, owning, or trading these substances is difficult due to many regulations and controls (Calderon et al., 2018; Pentney, 2001).

Thus, these controlled substances are commercially available to a very limited extent, and extensive restrictions are accompanied by import and export regulations to permit its handling. Moreover, their preparation requires secured environments and dedicated permits not only for the institution but also for the preparation of a specific compound.

The compounds represented by FIG. 1 for use in substance-assisted therapy can contain such a controlled compound in a chemically bound form as a prodrug. The classical route to access these compounds usually starts by preparing the controlled compound and then derivatizing it to the corresponding prodrug.

The above regulations and severe restrictions can be time-consuming and contribute to the overhead costs, regulatory resources, and additional expenses and permitting depending on the route chosen to manufacture the entactogenic prodrugs of this invention.

The present invention solves this practical problem by providing for a synthesis of substances with MDMA-like effects that are not scheduled in many countries or that are less regulated that MDMA. This can facilitate trading and use of these substances. Additionally, the present invention offers approaches to synthesize the MDMA-like non-controlled substances from non-controlled precursors and without producing scheduled substances in the process of synthesis. The present invention includes approaches to many MDMA-like prodrugs including the production of compound substances comprising a psychoactive base substance and attached to it an amino-acid to make the prodrug with a modified pharmacological behavior as described in U.S. Provisional Patent Application No. 63/115,245, filed Nov. 18, 2020.

The present invention also includes the example synthesis and synthetic pathway description of two such compound substances including lysMDMA and lysMDA. Three approaches are described including 1) the synthesis of lysMDMA or lysMDA from the controlled substances MDMA and MDA to produce non-controlled lysMDMA and lysMDA, respectively, 2) an approach starting from non-controlled precursors and producing a non-controlled compound (non-psychoactive precursor linked to amino acid) which is then converted into the final psychoactive substance without producing MDMA or MDA at any step, 3) N-diversification of lysMDA produced by either approach 1 or 2 and producing lysMDMA from lysMDA. Approach 3 can also be used to produce other MDMA-like substances like lysMDEA.

Approach 3 is a parallel approach allowing for synthesis of an entactogenic prodrug and applying a diversification late in the synthetic route to make other prodrugs. Such a diversification consists of a precedent preparation of, e.g., a late-stage intermediate of the prodrug lysMDA, and subsequent N-alkylation of these intermediates. This is not only advantageous in preventing the use or the preparation of several controlled compounds such as MDA, MDMA and MDEA, but also significantly reduces synthetic efforts to access the final prodrugs, a general advantage of a parallel approach in organic or medicinal chemistry.

When required to prepare several analogs or homologs, it can also be advantageous to use one controlled starting or intermediate material by preparing an appropriate intermediate being accessible to a chemical diversification. By such, only one controlled compound will be necessary to access several prodrugs. As an example, from an MDA intermediate several entactogenic prodrugs such as lysMDA, lysMDMA, or lysMDEA can be accessed The benefits of the present invention depend on country-specific scheduling of MDMA-like substances and are greatest in countries where substances such as lysMDMA are not scheduled as compared to MDMA being a narcotic and typically highly controlled substance.

Preparation of the Compounds

Figure 4:
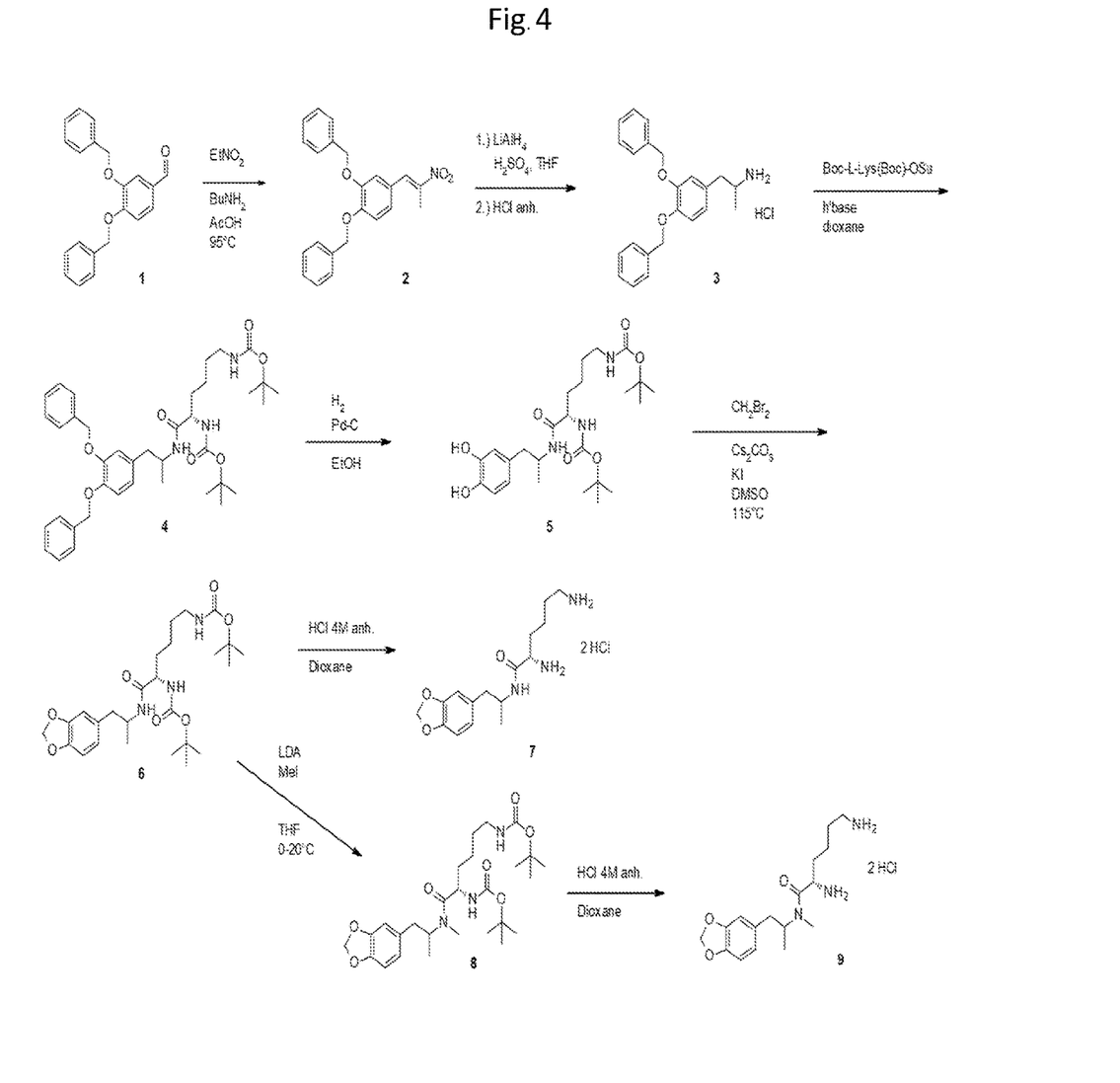
FIG. 4 shows the synthetic route to the prodrugs L-Lys-(R,S)-MDA (7) and L-Lys-(R,S)-MDMA (9) by omitting controlled psychoactive intermediates.

FIG. 4 summarily describes a general access, outlined to representative examples, namely the prodrugs L-Lys-(R,S)-MDA (7) and L-Lys-(R,S)-MDMA (9) by omitting controlled psychoactive intermediates. The corresponding benzaldehydes (compound 1 in FIG. 4) are either accessed by known procedures or are commercially available and then subjected to an aldol condensation, namely the Henry reaction, by mixing any of these aldehydes with a nitroalkane such as nitromethane, nitroethane or 1-nitropropane and a catalyst such as an organic salt or a mixture of an organic base and an organic acid, most favorably n-butylamine and acetic acid, such as illustrated in FIG. 4. The mixture can or not then be treated with heat in absence or presence of a drying agent such as an inorganic salt or, most favorably, molecular sieves. The water formed can also be removed azeotropically during reaction. The reaction mixture can be cooled, and the product solids formed can be filtered off, or the mixture can be concentrated in vacuo prior further treatment. The obtained residue can be further purified by crystallization or recrystallization or by column chromatography to get the final nitroolefins such as 2 as illustrated in FIG. 4.

As such, the obtained nitroalkenes are dissolved in an inert solvent such as tetrahydrofuran or diethyl ether and added to a suspension of alane generated in situ from allowing to react lithium aluminum hydride ($LiAlH_4$) with concentrated sulfuric acid ($H_2SO_4$) in a similar solvent (such as illustrated in FIG. 4). The reaction temperature can be set between −20° C. and 70° C., favorably at 0° C.-60° C. The reaction mixture is then quenched subsequently with an alcohol, favorably isopropanol, and then with a base such as aqueous sodium hydroxide before filtering it off. The filtrate is concentrated in vacuo and during the process an inert gas such as argon or nitrogen can be applied to prevent any carbamate formation. The residual amine-free base is then dissolved in a solvent, favorably non-protic, most favorably in diethyl ether or dioxane, and neutralized by the addition of anhydrous hydrogen chloride or sulfuric acid or any other salt forming organic agent such as fumaric acid, tartaric acid, or acetic acid in a similar solvent, to generate a salt, such as compound 3 as illustrated in FIG. 4.

Next, as illustrated in FIG. 4, bis-N,N'-protected lysine or another amino acid is activated at the carboxyl group by introducing a leaving group such as O-succinimide. This reagent is also widely commercially available. In the present example, this activated lysine derivative is allowed to react with a primary or secondary amine such as illustrated in FIG. 4, e.g., compound 3, to form the corresponding amide in the presence of a suitable non-protic base such as triethylamine, N-methylmorpholine or diisopropylethylamine (DIPEA, Hunig's base). Tetrahydrofuran or dioxane is used as a suitable solvent, but others such as dimethylformamide or dimethylsulfoxide may also be considered. The primary or secondary amine to be used for amide coupling with the amino acid can also be obtained by other synthetic procedures and is not limited by the access exhibited in FIG. 4.

After isolation and purification, the compounds such as bis-N,N'-protected compound 4 are redissolved in a suitable solvent such as an aqueous or non-aqueous alcohol such as methanol, ethanol, or isopropanol, or any other suitable organic or non-organic solvent, and are treated in such a way, that the chosen chemical substituents of the non-controlled compound, e.g., rising from compound 4, are converted to the desired substituents of the final prodrug. This chemical transformation can be done at any chemical step to prevent accumulation of a controlled compound and is not limited to what is exhibited in FIG. 4. As illustrated in FIG. 4, this can, as an example, be done by hydrogenolytic removal of the two O-benzyl groups using a suitable Hydrogen source and a suitable catalyst such as palladium on charcoal to get the dihydroxy compound 5. The derivative 5 can then be O,O'-methylenated with $CH_2Br_2$ or any other suitable reagent. In the present example, $CH_2Br_2$ was used, cesium carbonate served as base, potassium iodide was used as a Finkelstein-reaction-type catalyst and dimethyl sulfoxide served as suitable solvent. Any other appropriate conditions can be used and are not limited.

The bis-N,N'-protected intermediate 6 obtained from the above treatment is then treated with the corresponding conditions to allow deprotection, e.g., the use of an acid to remove tert-butoxycarbonyl groups or hydrogen in the presence of a catalyst such as palladium on activated charcoal to remove hydrogen-sensitive protecting groups. As illustrated in FIG. 4, anhydrous HCl in dioxane was used to access an illustrative final prodrug, namely lysMDA (7). The final products can either be isolated as a salt from corresponding conditions or as their free base. In an optional further purification step and/or conversion to a salt such as hydrochlorides or mesylates by known procedures will lead to the final products such as lysMDA dihydrochloride (7).

Secondary amides such as compound 6 can be used for further derivatization and to significantly reduce synthetic efforts, as outlined in FIG. 4. Specifically, compounds such as 6 can be alkylated at the amide nitrogen to get access to N-alkylated prodrugs such as lysMDMA (9), e.g., by reaction under suitable conditions such as deprotonating the amide with a base such as lithium diisopropylamide and then treating the intermediate with an alkylating agent such as methyl iodide in an appropriate solvent such as THF.

In such away, the obtained N-amide-alkylated bis-N,N'-protected intermediate (e.g., intermediate 8 in FIG. 4) can then be deprotected in a similar way as described before, to get access to final prodrugs such as lysMDMA (compound 9).

Figure 5:
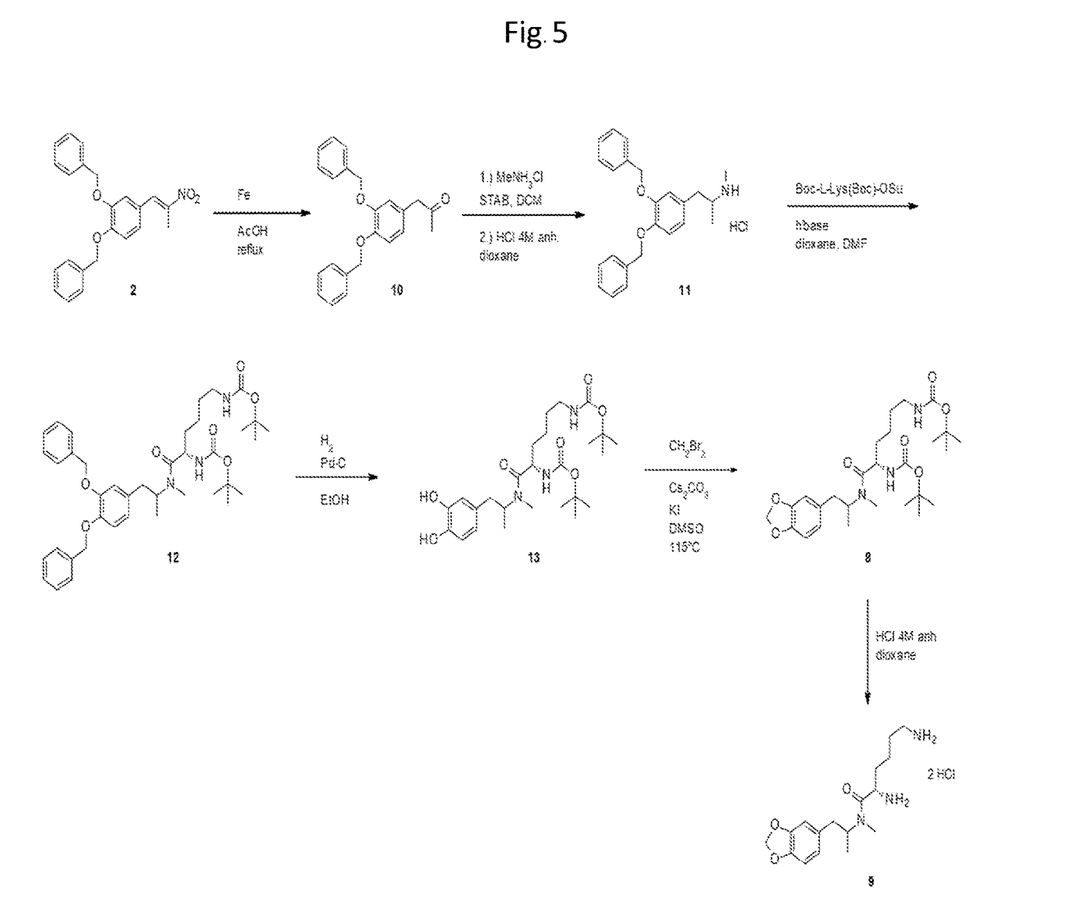
FIG. 5 shows another synthetic route to the prodrug lysMDMA (9) by omitting controlled psychoactive intermediates.

FIG. 5 summarily describes another synthetic route to prodrugs, exemplified on lysMDMA (9) by omitting controlled psychoactive intermediates. As such, a non-controlled and/or non-psychoactive suitable compound is first accessed. As an illustrative example, FIG. 5 outlines the access from the nitroolefin 2 obtained as described in FIG. 4: compound 2 is reduced to a ketone by using conditions such as a reducing agent in an appropriate solvent. Specifically, but not limited, this has been performed using iron in boiling glacial acetic acid. The resulting ketone 10 is then transferred to an appropriate primary or secondary amine, by applying reductive amination conditions. As an illustrative example, the N-methylated derivative 11 can be obtained in high yield by using dichloromethane (DCM) as solvent, sodium triacetoxyborohydride ($NaBH(OAc)_3$); STAB) as the reductive agent and methylamine hydrochloride as the amine source. Any other suitable solvent, amine source and reducing agent can be used and is not limited to what is represented in FIG. 5.

When having the corresponding primary or secondary amine such as compound 11 (FIG. 5), this can then be treated like what has been described in detail before for FIG. 4. As an illustrative example in FIG. 5, compound 11 was coupled with Boc-Lys(Boc)-OSu using Hunig's base and dioxane as well as dimethylformamide as co-solvent to get compound 12.

As a further illustration of the scope of invention, the obtained bis-N,N'-protected derivative 12 is then subjected to transformation of the aryl substituents: in such a way, the chosen chemical substituents of the non-controlled compound, e.g., rising from compound 11, are converted to the desired substituents of the final prodrug. This chemical transformation can be done at any chemical step to prevent accumulation of a controlled compound and is not limited to what is outlined in FIG. 5. As illustrated in FIG. 5, this can, as an example, be done by hydrogenolytic removal of the two O-benzyl groups using a suitable hydrogen source and a suitable catalyst such as palladium on charcoal to get the dihydroxy compound 13. The derivative 13 can then be O,O'-methylenated with $CH_2Br_2$ or any other suitable reagent. In the present example, $CH_2Br_2$ was used, cesium carbonate served as base, potassium iodide was used as a Finkelstein reaction-type catalyst and dimethyl sulfoxide served as suitable solvent. Any other appropriate conditions can be used, and the conditions used are not limiting the scope of invention.

The bis-N,N'-protected intermediate 8 obtained from the above treatment is then treated with the corresponding conditions to allow deprotection, e.g., the use of an acid to remove tert-butoxycarbonyl groups or hydrogen in the presence of a catalyst such as palladium on activated charcoal to remove hydrogen-sensitive protecting groups. As illustrated in FIG. 5, anhydrous HCl in dioxane was used to access an illustrative final prodrug, namely lysMDMA (9). The final products can either be isolated as a salt from corresponding conditions or as their free base. In an optional further purification step and/or conversion to a salt such as hydrochlorides or mesylates by known procedures will lead to the final products such as lysMDMA dihydrochloride (9).

Figure 6:
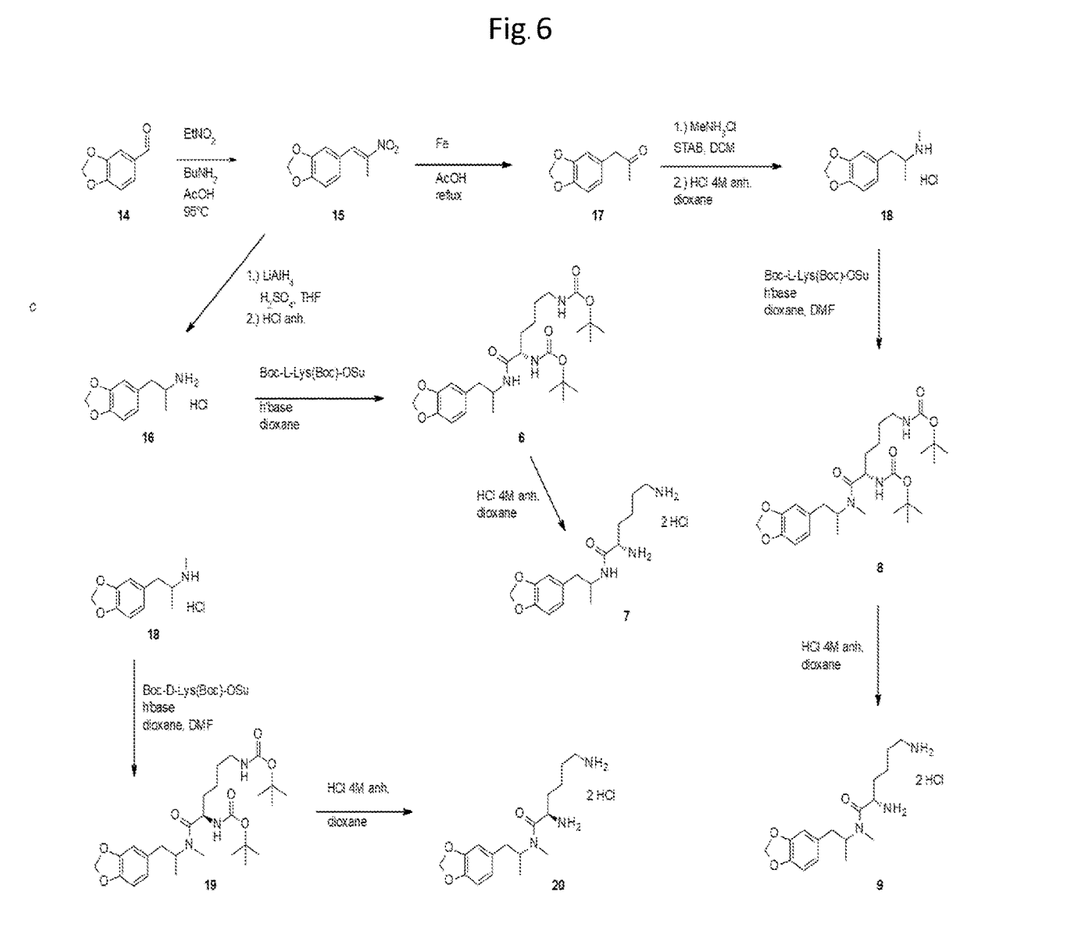
FIG. 6 shows the synthetic route to the prodrugs L-Lys-(R,S)-MDA (7) and L-Lys-(R,S)-MDMA (9) as well as to D-Lys-(R,S)-MDMA (20) by using controlled psychoactive intermediates (namely MDA, 16 and MDMA, 18, respectively).

FIG. 6 summarily describes a synthetic route to prodrugs such as L-Lys-(R,S)-MDA (7) and L-Lys-(R,S)-MDMA (9) as well as to D-Lys-(R,S)-MDMA (20) by using controlled psychoactive intermediates (MDA, 16 and MDMA, 18, respectively). As illustrative examples, the controlled compound MDA (16) was accessed by condensing piperonal (14) with nitroethane under catalytic conditions (n-butylamine and acetic acid) under heating and using molecular sieves, and subsequent reduction of the obtained nitroolefin 15 with LiAlH$_4$ in THF. The obtained free base of MDA (16) was converted to its hydrochloride salt for easier handling and additional purification. To access the controlled compound MDMA (18), we applied the same illustrative conditions developed for accessing compound 11 in FIG. 5: nitroolefin 15 was reduced to the ketone 17 using iron and glacial acetic acid (FIG. 6) and getting the N-methylated derivative 18 (MDMA hydrochloride) in high yield was achieved by using dichloromethane (DCM) as solvent, sodium triacetoxyborohydride (NaBH(OAc)$_3$; STAB) as the reductive agent and methylamine hydrochloride as the amine source. Any other suitable solvent, amine source and reducing agent can be used and is not limited to what is represented in FIG. 6.

Next, MDA hydrochloride (16) and MDMA hydrochloride (18) were converted to the corresponding N,N'-bis-protected amide derivatives 6 and 8, respectively (FIG. 6), under similar reaction conditions as described for compound 4 in FIG. 4 or for compound 12 in FIG. 5. The amines 16 and 18 are representative examples of controlled drugs and are not limited to be used in their salt forms. Any other salt or the use as free base can be applied to access the corresponding prodrug or intermediates to access them.

The N,N'-bis-protected amide derivatives 6 and 8, respectively can then be deprotected under conditions similar to what was described for accessing compound 7 from 6 (FIG. 4) and 9 from 8 (FIG. 5), respectively, to access lysMDA (7) and lysMDMA (9) (FIG. 6).

To access a prodrug containing an unnatural amino acid, e.g., an amino acid with D configuration, a corresponding activated and suitably protected amino acid can be used. As an illustrative example, D-lysMDMA (20) could be accessed from allowing to react MDMA (9) with Boc-D-Lys(Boc)-OSu using Hunig's base and dioxane as well as dimethylformamide as co-solvent to get intermediate compound 19, which was finally deprotected under conditions described before to get compound 20 (FIG. 6).

The prodrug compounds described herein are amides broken down by amidases in the human body to liberate the psychoactive base compound. There are possible stereoselective difference in metabolism rates of the compounds depending on the enantiomer used. The liberation rate of the psychoactive base compound, e.g., MDMA, can not only be triggered by the chiral center of the amino acid part but also by the chiral configuration of the parent drug, e.g., MDMA. This offers the creation of different pharmacokinetic profiles within the present invention depending on the type of enantiomer produced.

The chemical synthesis typically results in the compounds as racemates with different enantiomers present. It is important to know and determine the configuration of the amino acid part as well as the exact ratio of the contained psychoactive base compound's enantiomers, namely how much R-MDMA and S-MDMA are effectively contained in a product because different in vivo pharmacological properties will result depending on the stereochemistry of the substances. Usually, for MDMA synthesis a racemate (1:1 ratio) is formed under non-stereospecific or non-stereoselective conditions. Since a slight difference in the solubilities of the lysMDMA epimers was observed, it was desired to ensure there was no unwanted removal or reduction of one of the epimers (namely L-Lys-(R)-MDMA and L-Lys-(S)-MDMA). In addition to that, in some manufacturing procedures, high reaction temperatures (up to 115° C.) were applied, potentially facilitating an amino acid epimerization and thus a possible epimerization towards a total of four stereoisomers (D-Lys-(R)-MDMA and D-Lys-(S)-MDMA in addition to the aforementioned two stereoisomers) (this could also occur during the coupling reaction). To prove the robustness of the manufacturing process, two different chiral HPLC analyses were developed. With this, for the described synthetic routes it could be ensured that the final prodrugs contain a well-defined and a desired epimeric ratio and no unwanted separation or epimerization occurred. All these considerations are part of the synthetic approach quality assurance and part of the invention.

Examples 1-(3,4-Dibenzyloxyphenyl)-2-nitropropene, 2. A mixture of 20 g (62.8 mmol) 3,4-dibenzyloxybenzaldehyde (1) in 25 mL nitroethane was warmed until a clear solution was formed. Next, 8 g molecular sieves 3A, 1.0 mL n-butylamine and 1.0 mL acetic acid was added, and the mixture was gently stirred at 95° C. under nitrogen atmosphere. When the reaction was complete (30 minutes, monitoring by TLC, dichloromethane) the mixture was separated from the molecular sieves and concentrated in vacuo. The solid, dark-yellow residue was suspended in 50 mL isopropanol and stirred for a few minutes at ambient temperature before it was filtered off and rinsed with a minimal amount of cold isopropanol. The beige-yellow crystals were dried in vacuo at 45° C. to get 21.6 g (91.6%) 2. $^1$H-NMR (CDCl$_3$): 2.33 (d, MeC), 5.23 (s, CH$_2$O), 5.26 (s, CH$_2$O), 6.99-7.06 (m, 3 arom. H), 7.3-7.5 (m, 10 arom. H), 8.00 (s, CH=C).

3,4-Dibenzyloxyamphetamine hydrochloride (3,4-DBnA HCl), 3. To an ice-cooled suspension of 7.58 g (200 mmol) lithium aluminum hydride (LiAlH$_4$) in 160 mL tetrahydrofuran (THF) anhydr. was added dropwise 5.26 mL sulfuric acid (H$_2$SO$_4$) 97-99% under an inert atmosphere and vigorous stirring. When hydrogen evolution had ceased the mixture was stirred for another 5-10 minutes. Next, a solution of 20.0 g (53.3 mmol) 1-(3,4-dibenzyloxyphenyl)-2-nitropropene (2) in 80 mL THF anhydr. was added under ice-cooling at such a rate that the reaction became not too violent, and the reaction temperature stayed below 20-30° C. After completion of addition the mixture was brought to a gentle reflux for 3-5 minutes, and then again cooled with an ice-bath. Next, the mixture was cautiously quenched by successive and dropwise addition of 31.5 mL anhydr. isopropanol (IPA) and then 24.1 mL 2M sodium hydroxide solution (NaOH). Occasionally, THF was added to keep the mixture stirrable. When hydrolysis was complete, the mixture was filtered off and the filter cake was rinsed well with 2×100 mL diethyl ether ($Et_2O$). The filtrate was concentrated in vacuo to get 16.3 g crude amine as free base; purging the apparatus was performed by applying an inert gas such as nitrogen or argon which prevented the formation of any unwanted carbamates. The base was dissolved in 290 mL anhydr. diethyl ether containing 0.5% anhydr. IPA. The well stirred solution was cautiously neutralized by the addition of 2M anhydr. HCl in diethyl ether and occasional cooling; the pH should not be far from neutral to not get a sticky mass during processing. The suspension obtained was filtered off, rinsed with diethyl ether, and dried in vacuo to get 16.14 g (79%) of the hydrochloride product 3 as a white solid. $^1$H-NMR ($D_2O$): 1.05 (d, MeCH), 2.57 (m, 1 $ArCH_2$), 2.79 (m, 1 $ArCH_2$), 3.30 (m, $CHNH_3^+$), 4.77 (s, $CH_2O$), 4.87 (s, $CH_2O$), 6.60-6.77 (m, 3 arom. H), 7.0-7.3 (m, 10 arom. H).

3,4-Dibenzyloxyphenylacetone, 10. A suspension of 38.1 g (682 mmol) iron powder (<212 μm particle size) in 200 mL glacial acetic acid was heated to a gentle gas evolution (~95° C.) under mechanical stirring. Next, a warmed solution (~50° C.) of 21.6 g (57.5 mmol) 1-(3,4-dibenzyloxyphenyl)-2-nitropropene (2) in 150 mL glacial acetic acid was added over the course of 10 minutes. After another 10 minutes the reaction was complete (TLC:DCM) and the suspension was allowed to cool to ambient temperature. Water (150 mL) was added, and the mixture was extracted 3× with dichloromethane (DCM). The combined org. layers were washed with NaOH 2M (3×; until pH reached 10-12), dried over $MgSO_4$ and concentrated in vacuo. The oily residue (19.7 g) was purified by silica gel chromatography using hexane/ethyl acetate 3:1 to 1:1. Yield: 13.7 g (68.9%) product 10 as a slight yellowish oil. $^1$H-NMR ($CDCl_3$): 2.11 (s, MeC), 3.59 (s, $ArCH_2CO$), 5.17 (s, 2×$CH_2O$), 6.74 (d×d, 1 arom. H), 6.80 (d, 1 arom. H), 6.90 (d, 1 arom. H), 7.3-7.5 (m, 10 arom. H).

3,4-Dibenzyloxymethamphetamine hydrochloride (3,4-DBnMA HCl), 11. To a solution of 10.2 g (29.4 mmol) 3,4-dibenzyloxyphenylacetone (10) in 100 mL anhydr. DCM was added subsequently 2.09 g (30.9 mmol) methylamine hydrochloride, 5.38 mL (30.9 mmol) N,N-diisopropylethylamine (DIPEA) and 9.36 g (44.2 mmol) sodium triacetoxyborohydride ($NaBH(OAc)_3$; STAB). The mixture was stirred under nitrogen at ambient temperature overnight before it was diluted with 150 mL DCM and 100 mL water. The pH was adjusted to 12 by adding 2M NaOH, the layers were separated, and the aq. layer was further extracted 3× with DCM. The org. layers were combined, dried over $MgSO_4$ and concentrated in vacuo. The residual oil was co-evaporated 3× with hexane to remove any residual DIPEA. The base was dissolved in 100 mL anhydr. diethyl ether containing 0.5% anhydr. IPA. The well stirred solution was cautiously neutralized by the addition of 2M anhydr. HCl in diethyl ether and occasional cooling; the pH should not be far from neutral to not get a sticky mass during processing. The suspension obtained was filtered off, rinsed with diethyl ether, and dried in vacuo to get 10.45 g (89.2%) of the hydrochloride product 11 as a white solid. $^1$H-NMR ($D_2O$): 0.85 (d, MeCH), 2.46 (m, 1 $ArCH_2$), 2.54 (s, MeNH), 2.85 (m, 1 $ArCH_2$), 3.10 (m, $CHNH_{3+}$), 4.65 (s, $CH_2O$), 4.82 (s, $CH_2O$), 6.52-6.70 (m, 3 arom. H), 6.9-7.2 (m, 10 arom. H).

Boc-L-Lys(Boc)-3,4-dibenzyloxyamphetamine, 4. To a stirred mixture of 3.47 g (10.0 mmol) 3,4-dibenzyloxyamphetamine hydrochloride (3) and 2.18 mL (1.25 eq) DIPEA in 30 mL dioxane anhydr. under nitrogen were added 4.43 g (10.0 mmol) Boc-L-Lys(Boc)-OSu all at once. There was only a very slight increase in temperature recorded and the solids became all dissolved within 1-2 minutes. The clear solution was allowed to stir for 45 minutes. Next, the mixture was concentrated in vacuo, and the clear sticky residue was partitioned between 250 mL EtOAc and 100 mL water. The layers were separated, and the org. layer was further washed with water (2×50 mL), citric acid 5% (3×50 mL) and again with water (2×50 mL) and finally with brine (1×50 mL), dried over $MgSO_4$ and concentrated in vacuo to get a white solid which was further dried on h.v. Yield: 6.47 g 4. $^1$H-NMR (DMSO-$d_6$): 0.97 (d×d, 3H), 1.05-1.5 (m, 24H), 2.5-2.9 (m, 4H), 3.75-4.0 (m, 2H), 5.04-5.13 (m, 2×$CH_2O$), 6.4-6.8 (m, 3H), 6.9-7.0 (m, 2H), 7.3-7.5 (m, 10 arom. H), 7.63 (t, 1H). LCMS: $[M+1]^+$=676.88, found: 676.66.

Boc-L-Lys(Boc)-3,4-dihydroxyamphetamine, 5. The bis-0,0'-benzyl derivative 4 (6.40 g; 9.47 mmol) was dissolved in 190 mL ethanol (EtOH) abs. under warming in a nitrogen atmosphere. The clear solution was cooled to room temperature and 470 mg Pd—C 10% (dry) was added. The gaseous layer was exchanged from nitrogen to hydrogen by the vacuumization/venting method (3×) and the mixture was hydrogenated under vigorous stirring for 95 minutes using a $H_2$ balloon. After completion of reaction the mixture was filtered through a celite pad, the pad was rinsed with EtOH (2×30 mL), and the combined filtrates were concentrated in vacuo to get 4.38 g (93.3%) product 5 as a grey foam. $^1$H-NMR (DMSO-$d_6$, T=75° C.): 0.95-1.7 (m, 27H), 2.42 (m, 1H), 2.63 (m, 1H), 2.93 (m, 2H), 3.08 (bs, 1H), 3.79-3.95 (m, 2H), 6.2-6.4 (2×bm, 2H), 6.43 (m, 1H), 6.60 (m, 1H), 6.64 (d×d, 1H), 7.32 (t, 1H), 8.3 (bs, 2H). LCMS: $[M+1]^+$=496.63, found: 496.52.

Boc-L-Lys(Boc)-3,4-methylenedioxyamphetamine, 6, via ring closure. To a stirred mixture of 3.40 g (6.86 mmol) Boc-L-Lys(Boc)-3,4-dihydroxyamphetamine (5), 70 mg potassium iodide and 3.58 g (10.98 mmol) $Cs_2CO_3$ in 20 mL DMSO anhydr. was added 0.958 mL (13.72 mmol) $CH_2Br_2$ under $N_2$. The mixture was heated to 115° C. (preheated oil bath) for 65 minutes. Next, the mixture was cooled with an ice bath, diluted with 30 mL water, and extracted with 70 mL ethyl acetate/hexane 1:1. The aq. layer was further extracted once with 20 mL ethyl acetate/hexane 1:1. The combined org. layers were washed with water (1×20 mL), NaOH 2M (2×20 mL), citric acid 10% (2×20 mL) and water (1×20 mL), dried over $Na_2SO_4$ and then concentrated in vacuo. The residue was redissolved in a minimal amount of ethyl acetate and purified on a silica gel dry-flash column (diameter: 6 cm, height: 3.5 cm) by eluting with EtOAc:/hexane 1:1. Yield: 2.12 g (60.9%) product 6 as a yellowish viscous, sticky oil that solidified to a hard white wax overnight. $^1$H-NMR (DMSO-$d_6$, T=75° C.): 1.04 (m, 3H), 1.1-1.6 (m, 24H), 2.52-2.75 (m, 2H), 2.92 (m, 2H), 3.83 (m, 1H), 3.94 (m, 1H), 5.94 (m, 2H), 6.15-6.45 (2×bm, 2H), 6.63-6.68 (m, 1H), 6.73-6.79 (m, 2H), 7.35 (m, 1H). LCMS: $[M+1]^+$=508.64, found: 508.55.

Boc-L-Lys(Boc)-3,4-dibenzyloxymethamphetamine, 12. To a stirred mixture of 0.90 g (2.26 mmol) 3,4-dibenzyloxymethamphetamine hydrochloride (11) and 0.493 mL (1.25 eq) DIPEA in 10 mL dioxane anhydr. and 1 mL DMF anhydr. under nitrogen were added 1.00 g (2.26 mmol) Boc-L-Lys(Boc)-OSu all at once. The mixture remained as a suspension but dissolved progressively. After stirring overnight some 50% conversion was observed. To the mixture was added another 0.50 g Boc-L-Lys(Boc)-OSu and 0.49 mL DIPEA and after stirring at 50° C. for another night the reaction was complete. The dioxane was removed in vacuo and the residue was dissolved in EtOAc (25 mL) and washed with water (3×20 mL), citric acid 5% (1×20 mL) and water again (1×20 mL) and finally with brine (1×20 mL). The org. layer was dried over $Na_2SO_4$ and directly purged on a small silica-gel pad (diameter: 4 cm, height: 1 cm); a filter was used to prevent any disturbance of the silica gel. The liquid was sucked off and the pad was rinsed with enough ethyl acetate/hexane 1:1 to elute the product. The collected eluate was concentrated in vacuo to get 1.73 g product 12 as a highly viscous, orangish oil. $^1$H-NMR (DMSO-$d_6$, T=75° C.): even at elevated temperature this NMR spectrum remained complex. 1.0-1.7 (many overlayed signals), 2.6-3.2 (many overlayed signals), 3.8-4.9 (many overlayed signals), 5.04-5.11 (m, 2×$CH_2O$), 6.2-7.0 (many overlayed signals), 7.25-7.45 (m, 10 arom. H). LCMS: $[M+1]^+$= 690.91, found: 690.69.

Boc-L-Lys(Boc)-3,4-dihydroxymethamphetamine, 13. In analogy to what was described for the preparation of 5, from 1.70 g (2.46 mmol) Boc-L-Lys(Boc)-3,4-dibenzyloxymethamphetamine (12) and 120 mg Pd—C 10% (dry) in 50 mL EtOH abs. (22 h reaction time with $H_2$), there was obtained 1.22 g (97.3%) product 13 as a grey foam. $^1$H-NMR (DMSO-$d_6$, T=75° C.): even at elevated temperature this NMR spectrum remained complex. 1.0-1.7 (many overlayed signals), 2.5-3.2 (many overlayed signals), 3.8-4.8 (many overlayed signals), 6.1-6.7 (many overlayed signals), 8.1-8.6 (bs). LCMS: $[M+1]^+$=510.66, found: 510.56.

Boc-L-Lys(Boc)-3,4-methylenedioxymethamphetamine, 8, via ring closure. In analogy to what was described for the preparation and purification of 6, from 1.20 g (2.35 mmol) Boc-L-Lys(Boc)-3,4-dihydroxymethamphetamine (13), 1.23 g (3.77 mmol) $Cs_2CO_3$, 24 mg potassium iodide and 0.329 mL (4.70 mmol) $CH_2Br_2$ in 7 mL DMSO anhydr. (35 minutes reaction time) there was obtained 0.60 g (48.8%) 8 as a water-clear sticky mass. $^1$H-NMR (DMSO-$d_6$, T=75° C.): even at elevated temperature this NMR spectrum remained complex. 1.0-1.6 (many overlayed signals), 2.6-3.0 (many overlayed signals), 4.1-4.3 (broad overlayed signals), 4.8 (broad signal(s)), 5.93 (m, $OCH_2O$, 2H), 6.1-6.5 (overlayed signals), 6.65 (m, 1 arom. H), 6.75 (m, 2 arom. H). LCMS: $[M+1]^+$=522.67, found: 522.59. Chiral HPLC analysis results of the product: see section "Chiral HPLC analysis of N,N'-bis-protected compounds".

Boc-L-Lys(Boc)-3,4-methylenedioxymethamphetamine, 8, via N-methylation. For an easier handling, a larger amount of fresh lithium diisopropylamide (LDA) was prepared (factor five): 2104 butyllithium (BuLi) 2.5M was added to a solution of 74.24 diisopropylamine in 2.5 mL THF at 0° C. under $N_2$. From this solution one fifth (0.56 mL; 1.05 eq; $v_{tot}$=approx. 2.8 mL) were added dropwise to a solution of 50.7 mg (0.1 mmol) Boc-L-Lys(Boc)-3,4-methylenedioxy-amphetamine (6) in 0.5 mL THF anhydr. under ice-cooling and $N_2$ atmosphere. After 10 minutes a solution of 6.22 µL (1.0 eq) methyl iodide in 0.1 mL THF anhydr. was added dropwise (1 minute). The mixture was progressively allowed to reach ambient temperature. An LCMS/UV analysis indicated identical retention time, UV spectrum and mass $[M+1]^+$ as observed when preparing the title compound either by coupling of MDMA HCl (18) with Boc-L-Lys(Boc)-OSu or by 0,0'-methylation of Boc-L-Lys(Boc)-3,4-dihydroxymethamphetamine (13) with $CH_2Br_2$.

1-(3,4-Methylenedioxyphenyl)-2-nitropropene, 15. In analogy to what was described for the preparation and purification of 2, from 200 g (1.33 mol) piperonal, 170 g molecular sieves 3 Å, 21 mL n-butylamine and 21 mL acetic acid in 530 mL nitroethane (70 minutes at 95° C.), there were obtained 221.7 g (80.5%) product 15 as bright yellow crystals. $^1$H-NMR ($CDCl_3$): 2.46 (d, MeC), 6.04 (s, $OCH_2O$), 6.89 (d, 1 arom. H), 6.94 (d, 1 arom. H), 6.98 (d×d, 1 arom. H), 8.02 (s, CH=C).

3,4-Methylenedioxyamphetamine hydrochloride (MDA HCl), 16. In analogy to what was described for the preparation and purification of 3, from 37.8 g (0.995 mol) $LiAlH_4$ in 780 mL THF anhydr., 26.3 mL $H_2SO_4$ 97-99%, a solution of 55.0 g (0.265 mol) 1-(3,4-methylenedioxyphenyl)-2-nitropropene (15) in 380 mL THF anhydr. and reaction hydrolysis with 157 mL anhydr. IPA and 120 mL 2M NaOH solution, there were obtained 44 g MDA free base as an orange oil. The base was converted to its hydrochloride salt from dissolving it in 1.3 L anhydr. diethyl ether containing 0.5% anhydr. IPA and neutralizing it by addition of 2M anhydr. HCl in diethyl ether in a similar way as described for 3. Yield: 39.4 g (82.9%) MDA hydrochloride (16) as a white solid. $^1$H-NMR ($D_2O$): 1.31 (d, MeCH), 2.88 (m, 2 $ArCH_2$), 3.62 (m, $CHNH_{3+}$), 6.01 (s, $OCH_2O$), 6.71 (d×d, 1 arom. H), 6.87 (d, 1 arom. H), 6.91 (d, 1 arom. H).

3,4-methylenedioxyphenylacetone, 17. In analogy to what was described for the preparation of 10, from 288 g (5.15 mol) iron powder in 900 mL glacial acetic acid and a warmed solution (~50° C.) of 90 g (434 mmol) 1-(3,4-methylenedioxyphenyl)-2-nitropropene (15) in 300 mL glacial acetic acid, there was obtained 72.6 g crude product as an orange oil. This was further purified by vacuum distillation (0.6-0.8 mbar, head temperature approx. 105° C.) to get 63.2 g (81.6%) product 17 as a slight yellowish oil. $^1$H-NMR ($CDCl_3$): 2.17 (s, MeC), 3.62 (s, $ArCH_2CO$), 5.96 (s, $OCH_2O$), 6.66 (d×d, 1 arom. H), 6.70 (d, 1 arom. H), 6.79 (d, 1 arom. H).

3,4-Methylenedioxymethamphetamine hydrochloride (MDMA HCl), 18. In analogy to what was described for the preparation of 11, from 70.0 g (392.8 mmol) 3,4-methylenedioxyphenylacetone (17), 27.9 g (412.5 mmol) methylamine hydrochloride, 72 mL (412.5 mmol) DIPEA and 125 g (589.3 mmol) $NaBH(OAc)_3$ in 700 mL anhydr. DCM (slight exothermic reaction, thus the reaction flask was ice-cooled for the first hour down to approx. 20° C.), there were obtained 80 g of MDMA free base as a yellow oil. This was further purified by vacuum distillation (0.2 mbar, head temperature approx. 95-105° C.) to get 70.0 g of pure MDMA free base which solidified to a white wax upon standing at ambient temperature. The solid was melted by using a heat gun, diluted with 13 mL IPA anhydr., and cooled further before the solution was dissolved in 700 mL anhydr. diethyl ether. The well stirred clear solution was cautiously neutralized by the addition of 2M anhydr. HCl in diethyl ether and occasional cooling; the pH should not be far from neutral to not get a sticky mass during processing. The suspension obtained was filtered off, rinsed with diethyl ether, and dried in vacuo at 40° C. to get 78.2 g (86.7%) MDMA hydrochloride (18) as a white solid. $^1$H-NMR ($D_2O$): 1.30 (d, MeCH), 2.72 (s, MeNH), 2.93 (d×m, $ArCH_2$), 3.51 (m, $CHNH_{3+}$), 5.99 (s, $OCH_2O$), 6.81 (d×d, 1 arom. H), 6.87 (d, 1 arom. H), 6.92 (d, 1 arom. H).

Boc-L-Lys(Boc)-3,4-methylenedioxyamphetamine, 6, from MDA. In analogy to what was described for the preparation of Boc-L-Lys(Boc)-3,4-dibenzyloxyamphetamine (4), from 18.0 g (83.5 mmol) 3,4-methylenedioxyamphetamine hydrochloride (16), 18.18 mL DIPEA and 46.27 g plus 4.7 g supplement (after 1.2 h reaction time) of Boc-L-Lys(Boc)-OSu in 250 mL dioxane anhydr. under nitrogen were obtained 55.0 g crude product as a white foam. This was further purified by chromatography on silica gel using DCM for coating on silica gel (to dryness) and using ethyl acetate/hexane as eluent. Yield: 48.1 g 6. An LCMS/UV analysis (retention time, UV spectrum and mass [M+1]$^+$) and $^1$H-NMR (DMSO-d$_6$, T=75° C.) was identical to what was observed when preparing the title compound by O,O'-methylenation of Boc-L-Lys(Boc)-3,4-dihydroxyamphetamine (5) with CH$_2$Br$_2$ (see corresponding ring closure experiment).

Boc-L-Lys(Boc)-3,4-methylenedioxymethamphetamine, 8, from MDMA. In analogy to what was described for the preparation of Boc-L-Lys(Boc)-3,4-dibenzyloxymethamphetamine (12), from 16.56 g (72.1 mmol) 3,4-methylenedioxymethamphetamine hydrochloride (18), 15.73 mL DIPEA and 40.0 g plus 12.8 g supplement (after 17 h reaction time) of Boc-L-Lys(Boc)-OSu in 230 mL dioxane anhydr. and 20 mL anhydr. DMF under nitrogen at ambient temperature (17 h) to 65° C. (9 h) were obtained 67 g crude product as a white foam. This was further purified by chromatography on silica gel using DCM for coating on silica gel (to dryness) and using ethyl acetate/hexane 1:4 as eluent. Yield: 33.6 g (89.3%) product 8 as a yellowish foam. An LCMS/UV analysis (retention time, UV spectrum and mass [M+1]$^+$) and $^1$H-NMR (DMSO-d$_6$, T=75° C.) as well as chiral HPLC analysis was identical to what was observed when preparing the title compound by O,O'-methylenation of Boc-L-Lys(Boc)-3,4-dihydroxymethamphetamine (13) with CH$_2$Br$_2$ (see corresponding ring closure experiment). Chiral HPLC analysis results of the product: see section "Chiral HPLC analysis of N,N'-bis-protected compounds".

Boc-D-Lys(Boc)-3,4-methylenedioxymethamphetamine, 19, from MDMA. The title compound was prepared in an identical manner as described for its L-Lys diastereomeric congeners (Boc-L-Lys(Boc)-3,4-methylenedioxymethamphetamine, 8) by using MDMA HCl (18) and Boc-D-Lys(Boc)-OSu. This was analyzed by LCMS (LCMS: [M+1]$^+$=522.67, found: 522.58) and chiral HPLC analysis; see section "Chiral HPLC analysis of N,N'-bis-protected compounds".

Chiral HPLC analysis of N,N'-bis-protected compounds. HPLC Agilent 1100; column: Macherey-Nagel column, NUCLEOCEL DELTA RP S, 250×4.6 mm, 5 μm; eluent: premixed in an A/B=50:50 ratio, with A: 0.05M TFA in H$_2$O, and B: acetonitrile; flow rate: 1.0 mL/min; column temperature: 20° C. (thermostat); injection volumes: 1 to 5 μL; detection: UV @ 210 nm and 286 nm. For compound Boc-L-Lys(Boc)-3,4-methylenedioxymethamphetamine (8) obtained by using MDMA HCl (18) and Boc-L-Lys(Boc)-OSu were obtained two baseline-separated peaks (retention times 13.6 minutes and 15.8 minutes) with an area ratio of 49.2:50.8. For compound Boc-L-Lys(Boc)-3,4-methylenedioxymethamphetamine (8) obtained by ring closure from Boc-L-Lys(Boc)-3,4-dihydroxymethamphetamine (13) and CH$_2$Br$_2$ were obtained two baseline-separated peaks (retention times 13.6 minutes and 15.8 minutes) with an area ratio of 49.5:50.5. For compound Boc-D-Lys(Boc)-3,4-methylenedioxymethamphetamine (19) obtained by using MDMA HCl (18) and Boc-D-Lys(Boc)-OSu was obtained one single peak (retention time 12.5 minutes) and thus no separation occurred by this method; for proof of non-epimerization and for a 1:1 diastereomeric ratio see section "Chiral HPLC analysis of the invented prodrugs (N,N'-bis-deprotected compounds)".

L-Lys-3,4-methylenedioxyamphetamine dihydrochloride (L-Lys-(R,S)-MDA*2 HCl), 7. The N,N'-deprotection was performed on Boc-L-Lys(Boc)-3,4-dihydroxyamphetamine (6) obtained either from 0,0'-methylenation of Boc-L-Lys(Boc)-3,4-dihydroxyamphetamine (5) with CH$_2$Br$_2$ (see ring closure experiment), or obtained from coupling of MDA HCl (16) with Boc-L-Lys(Boc)-OSu. This gave essentially identical LCMS/UV data (retention time, UV spectrum and mass [M+1]$^+$) and $^1$H-NMR data (DMSO-d$_6$, T=75° C.) for the title product 7. In a representative manner, to a solution of 47.0 g (92.6 mmol) Boc-L-Lys(Boc)-3,4-methylene-dioxyamphetamine (6) in 300 mL anhydr. dioxane under nitrogen were added 139 mL 4M HCl anhydr. in dioxane in one portion. The mixture was stirred at ambient temperature until completion of reaction (4 h). Next, the supernatant liquid layer was cautiously removed by decantation and the remaining sticky mass was rinsed by the addition and then decantation of another 150 mL fresh anhydr. dioxane. The remaining sticky residue was dried in vacuo to get an off-white crude product. This was dissolved in 130 mL IPA/MeOH 10:3 under warming and applying of an ultrasonic bath, before it was cooled to ambient temperature. The clear solution was added dropwise to 2 L of anhydr. Et$_2$O under vigorous stirring and under N$_2$ which caused a fine precipitation. After completion of addition the mixture was stirred for another hour before it was filtered of. The filter cake was rinsed with additional 400 mL anhydr. Et$_2$O and finally dried overnight at 35° C. in vacuo to get 26.3 g (74.4%) L-Lys-(R,S)-MDA*2 HCl (7) as a white powder. $^1$H-NMR (DMSO-d$_6$, T=75° C.), even at elevated temperature this NMR spectrum remained complex: 1.05-1.92 (many overlayed signals, 10H), 2.52-2.85 (many overlayed signals, 4H), 3.73 (t, 1H), 3.99 (m, 1H), 5.94-6.00 (m, OCH$_2$O, 2H), 6.67-6.73 (m, 1 arom. H), 6.78-6.83 (m, 2 arom. H), 8.23 (bs, several exchangeable H), 8.52 (m, 1H). LCMS: [M+1]$^+$=308.41, found: 308.35. HPLC (@195 nm): >99% purity.

L-Lys-3,4-methylenedioxymethamphetamine dihydrochloride (L-Lys-(R,S)-MDMA*2 HCl), 9. The N,N'-deprotection was performed on Boc-L-Lys(Boc)-3,4-methylenedioxymethamphetamine (8) obtained either from O,O'-methylenation of Boc-L-Lys(Boc)-3,4-dihydroxymethamphetamine (13) with CH$_2$Br$_2$ (see ring closure experiment), or obtained from coupling of MDMA HCl (18) with Boc-L-Lys(Boc)-OSu. This gave essentially identical LCMS/UV data (retention time, UV spectrum and mass [M+1]$^+$) and $^1$H-NMR data (DMSO-d$_6$, T=75° C.) as well as chiral HPLC analysis data for the title product 9. In a representative manner, to a solution of 33.0 g (63.3 mmol) Boc-L-Lys(Boc)-3,4-methylenedioxymethamphetamine (8) in 260 mL anhydr. dioxane under nitrogen were added 95 mL 4M HCl anhydr. in dioxane in one portion. The mixture was stirred at ambient temperature until completion of reaction (16 h). Next, the supernatant liquid layer was cautiously removed by decantation and the remaining sticky mass was rinsed by the addition and then decantation of another 100 mL fresh anhydr. dioxane. The remaining sticky residue was dried in vacuo to get an off-white crude product. This was dissolved in 90 mL IPA/MeOH 10:3 under warming and applying of an ultrasonic bath, before it was cooled to ambient temperature. The clear solution was added dropwise to 1.4 L of anhydr. Et$_2$O under vigorous stirring and under N$_2$ which caused a fine precipitation. After completion of addition the mixture was stirred for another hour before it was filtered of. The filter cake was rinsed with additional 300 mL anhydr. Et$_2$O and finally dried overnight at 35° C. in vacuo to get 20.3 g (81.5%) L-Lys-(R,S)-MDMA*2 HCl (9) as a white powder. $^1$H-NMR (DMSO-d$_6$, T=75° C.), even at elevated temperature this NMR spectrum remained complex and for some signals fractional integrals were observed: 1.03-1.92 (many overlayed signals), 2.60-2.95

(many overlayed signals), 3.42 (q), 3.75-4.25 (many overlayed signals), 4.58 (m), 4.88 (m), 5.94-6.20 (m, OCH$_2$O, 2H), 6.63-6.92 (m, 3 arom. H), 8.45 (bs, several exchangeable H). LCMS: [M+1]$^+$=322.43, found: 322.33. HPLC (@195 nm): >99% purity. Chiral HPLC analysis results of the products: see section "Chiral HPLC analysis of the invented prodrugs (N, N'-bis-deprotected compounds)".

D-Lys-3,4-methylenedioxymethamphetamine dihydrochloride (D-Lys-(R,S)-MDMA*2 HCl), 20. The title compound was prepared in an identical manner as described for its L-Lys diastereomeric congeners (L-Lys-(R,S)-MDMA*2 HCl; 9) by using Boc-D-Lys(Boc)-3,4-methylenedioxymethamphetamine (19) and gave identical LCMS data ([M+1]$^+$]$^+$=322.43, found: 322.34). Chiral HPLC analysis results of the product: see section "Chiral HPLC analysis of the invented prodrugs (N, N'-bis-deprotected compounds)".

Chiral HPLC analysis of the invented prodrugs (N,N'-bis-deprotected compounds). HPLC Agilent 1100; column: Macherey-Nagel EC100/4 Nucleodur C18 Gravity, 1.8 μm; eluent: premixed in an A/B=85:15 ratio, with A: 0.005M (1R)-(-)-10-camphorsulfonic acid ammonium salt in H$_2$O, plus H$_3$PO$_4$ adjusted to pH~2.1, and B: acetonitrile; flow rate: 1 mL/min; column temperature: 40° C.; injection volumes: 34 to 104; detection: UV @ 210 nm and 286 nm. For compound L-Lys-(R,S)-MDMA*2 HCl (9) obtained either by 1.) using Boc-L-Lys(Boc)-3,4-methylenedioxymethamphetamine (8) obtained from MDMA HCl (18) and Boc-L-Lys(Boc)-OSu or obtained by 2.) using Boc-L-Lys(Boc)-3,4-methylenedioxymethamphetamine (8) obtained from ring closure experiment (Boc-L-Lys(Boc)-3,4-dihydroxymethamphetamine (13) with CH$_2$Br$_2$) were obtained two baseline-separated peaks (retention times 9.2 minutes and 10.7 minutes) with an area ratio of ~48:52. For compound D-Lys-(R,S)-MDMA*2 HCl (20) obtained from Boc-D-Lys(Boc)-3,4-methylenedioxymethamphetamine (19) were obtained two baseline-separated peaks (retention times 9.0 minutes and 10.5 minutes) with an area ratio of ~47:53.

Summary of chiral HPLC analysis data. The use of a chiral HPLC column (see section "Chiral HPLC analysis of N,N'-bis-protected compounds") could satisfyingly separate the diastereomeric intermediates of Boc-L-Lys(Boc)-3,4-methylenedioxymethamphetamine (8); for the diastereomers of Boc-D-Lys(Boc)-3,4-methylenedioxymethamphetamine (19) there was, however, no separation observed. Nevertheless, for 19 (appeared as a single peak) was obtained a completely different retention time than for both diastereomers of 8 (appeared as two well separated peaks). With this, it was proven that 8 did not epimerize towards 19—provided that the obtained 19 effectively consists of two epimers (what has been proven in the following investigations):

On a non-chiral column, by using a chiral agent added to the eluent (see section "Chiral HPLC analysis of the invented prodrugs (N,N'-bis-deprotected compounds)", each diastereomeric pair of the N,N'-bis-deprotected compounds 9 and 20 could effectively be separated; diastereomeric ratios were 50:50 for both products. With this, the non-epimerization of each diastereomeric mixture during reaction conditions (e.g., amide coupling and N,N'-bis-deprotection) is ultimately proven.

An additional note has to be given in order to explain the necessity of the chiral HPLC analysis on both the N,N'-bis-protected compounds 8 and 19 as well as on both the N,N'-bis-deprotected compounds 9 and 20. Opposite to the investigations with Boc-L-Lys(Boc)-3,4-methylenedioxymethamphetamine (8; two peaks observed) and Boc-D-Lys(Boc)-3,4-methylenedioxymethamphetamine (19; one peak observed; and pre-mixing samples of both compounds 8 and 19 lead to three HPLC peaks), pre-mixing samples of L-Lys-(R,S)-MDMA (9; two HPLC peaks when analyzed separately) with D-Lys-(R,S)-MDMA (20; two HPLC peaks when analyzed separately) in about a 1:1 amount, leads to two HPLC peaks exclusively, indicating that each diastereomeric composition interacts identical with the HPLC column under the chosen conditions. Thus, in this case, both types of chiral HPLC analyses were necessary to prove the inertness of the molecules for not being susceptible to racemization or epimerization on either stereo center under the selected reaction and purification conditions.

Throughout this application, various publications, including United States patents, are referenced by author and year and patents by number. Full citations for the publications are listed below. The disclosures of these publications and patents in their entireties are hereby incorporated by reference into this application to more fully describe the state of the art to which this invention pertains.

The invention has been described in an illustrative manner, and it is to be understood that the terminology, which has been used is intended to be words of description rather than of limitation.

Obviously, many modifications and variations of the present invention are possible considering the above teachings. It is, therefore, to be understood that within the scope of the appended claims, the invention can be practiced otherwise than as specifically described.

REFERENCES

1. Baggott M J, Garrison K J, Coyle J R, Galloway G P, Barnes A J, Huestis M A, & Mendelson J E (2019). Effects of the Psychedelic Amphetamine MDA (3,4-Methylenedioxyamphetamine) in Healthy Volunteers. J Psychoactive Drugs 51: 108-117.
2. Calderon S N, Hunt J, & Klein M (2018). A regulatory perspective on the evaluation of hallucinogen drugs for human use. Neuropharmacology 142: 135-142.
3. Carhart-Harris R L, & Goodwin G M (2017). The therapeutic potential of psychedelic drugs: past, present, and future. Neuropsychopharmacology 42: 2105-2113.
4. Danforth A Exploring MDMA-assisted therapy as a new pathway to social adaptability for autistic adults.
5. Danforth A L, Grob C S, Struble C, Feduccia A A, Walker N, Jerome L, Yazar-Klosinski B, & Emerson A (2018). Reduction in social anxiety after MDMA-assisted psychotherapy with autistic adults: a randomized, double-blind, placebo-controlled pilot study. Psychopharmacology (Berl) 235: 3137-3148.
6. Danforth A L, Struble C M, Yazar-Klosinski B, & Grob C S (2016). MDMA-assisted therapy: A new treatment model for social anxiety in autistic adults. Prog Neuropsychopharmacol Biol Psychiatry 64: 237-249.
7. Holze F, Vizeli P, Muller F, Ley L, Duerig R, Varghese N, Eckert A, Borgwardt S, & Liechti M E (2020). Distinct acute effects of LSD, MDMA, and D-amphetamine in healthy subjects. Neuropsychopharmacology 45: 462-471.
8. Hysek C M, Schmid Y, Simmler L D, Domes G, Heinrichs M, Eisenegger C, Preller K H, Quednow B B, & Liechti M E (2014). MDMA enhances emotional empathy and prosocial behavior. Soc Cogn Affect Neurosci 9: 1645-1652.
9. Liechti M E (2017). Modern clinical research on LSD. Neuropsychopharmacology 42: 2114-2127.

10. Luethi D, Kolaczynska K E, Walter M, Suzuki M, Rice K C, Blough B E, Hoener M C, Baumann M H, & Liechti M E (2019). Metabolites of the ring-substituted stimulants MDMA, methylone and MDPV differentially affect human monoaminergic systems. J Psychopharmacol 33: 831-841.

11. Luoma J B, Chwyl C, Bathje G J, Davis A K, & Lancelotta R (2020). A Meta-Analysis of Placebo-Controlled Trials of Psychedelic-Assisted Therapy. J Psychoactive Drugs: 1-11.

12. Mitchell J M, Bogenschutz M, Lilienstein A, Harrison C, Kleiman S, Parker-Guilbert K, Ot'alora G M, Garas W, Paleos C, Gorman I, Nicholas C, Mithoefer M, Carlin S, Poulter B, Mithoefer A, Quevedo S, Wells G, Klaire S S, van der Kolk B, Tzarfaty K, Amiaz R, Worthy R, Shannon S, Woolley J D, Marta C, Gelfand Y, Hapke E, Amar S, Wallach Y, Brown R, Hamilton S, Wang J B, Coker A, Matthews R, de Boer A, Yazar-Klosinski B, Emerson A, & Doblin R (2021). MDMA-assisted therapy for severe PTSD: a randomized, double-blind, placebo-controlled phase 3 study. Nat Med 27: 1025-1033.

13. Mithoefer M C, Feduccia A A, Jerome L, Mithoefer A, Wagner M, Walsh Z, Hamilton S, Yazar-Klosinski B, Emerson A, & Doblin R (2019). MDMA-assisted psychotherapy for treatment of PTSD: study design and rationale for phase 3 trials based on pooled analysis of six phase 2 randomized controlled trials. Psychopharmacology (Berl).

14. Mithoefer M C, Wagner M T, Mithoefer A T, Jerome I, & Doblin R (2010). The safety and efficacy of ±3,4-methylenedioxymethamphetamine-assisted psychotherapy in subjects with chronic, treatment-resistant post-traumatic stress disorder: the first randomized controlled pilot study. J Psychopharmacol 25: 439-452.

15. Nichols D E, Johnson M W, & Nichols C D (2017). Psychedelics as medicines: an emerging new paradigm. Clin Pharmacol Ther 101: 209-219.

16. Oehen P, Traber R, Widmer V, & Schnyder U (2013). A randomized, controlled pilot study of MDMA (±3,4-methylenedioxymethamphetamine)-assisted psychotherapy for treatment of resistant, chronic post-traumatic stress disorder (PTSD). J Psychopharmacol 27: 40-52.

17. Oeri H E (2020). Beyond ecstasy: Alternative entactogens to 3,4-methylenedioxymethamphetamine with potential applications in psychotherapy. J Psychopharmacol: 269881120920420.

18. Pentney A R (2001). An exploration of the history and controversies surrounding MDMA and MDA. J Psychoactive Drugs 33: 213-221.

19. Rickli A, Hoener M C, & Liechti M E (2015a). Monoamine transporter and receptor interaction profiles of novel psychoactive substances: para-halogenated amphetamines and pyrovalerone cathinones. Eur Neuropsychopharmacol 25: 365-376.

20. Rickli A, Kopf S, Hoener M C, & Liechti M E (2015b). Pharmacological profile of novel psychoactive benzofurans. Br J Pharmacol 172: 3412-3425.

21. Sessa B, Higbed L, & Nutt D (2019). A Review of 3,4-methylenedioxymethamphetamine (MDMA)-Assisted Psychotherapy. Front Psychiatry 10: 138.

22. Simmler L, Buser T, Donzelli M, Schramm Y, Dieu L H, Huwyler J, Chaboz S, Hoener M, & Liechti M E (2013). Pharmacological characterization of designer cathinones in vitro. Br J Pharmacol 168: 458-470.

23. Trope A, Anderson B T, Hooker A R, Glick G, Stauffer C, & Woolley J D (2019). Psychedelic-Assisted Group Therapy: A Systematic Review. J Psychoactive Drugs 51: 174-188.

24. Yensen R, Di Leo F B, Rhead J C, Richards W A, Soskin R A, Turek B, & Kurland A A (1976). MDA-assisted psychotherapy with neurotic outpatients: a pilot study. J Nery Ment Dis 163:

What is claimed is:

1. A method of synthesizing a pharmacological compound substance including the steps of:
    performing an aldol condensation on 3,4-dibenzyloxybenzaldehyde to obtain 1-(3,4-Dibenzyloxyphenyl)-2-nitropropene;
    dissolving 1-(3,4-Dibenzyloxyphenyl)-2-nitropropene in an inert solvent, adding the solution to a suspension of alane, and obtaining 3,4-Dibenzyloxyamphetamine hydrochloride;
    reacting 3,4-Dibenzyloxyamphetamine hydrochloride with an activated lysine derivative to obtain Boc-L-Lys(Boc)-3,4-dibenzyloxyamphetamine;
    dissolving Boc-L-Lys(Boc)-3,4-dibenzyloxyamphetamine in a solvent and performing a hydrogenolytic removal of O-benzyl groups to obtain Boc-L-Lys(Boc)-3,4-dihydroxyamphetamine;
    O,O'—methylating Boc-L-Lys(Boc)-3,4-dihydroxyamphetamine to obtain Boc-L-Lys(Boc)-3,4-methylenedioxyamphetamine; and
    performing a step chosen from the group consisting of
    (A) deprotecting Boc-L-Lys(Boc)-3,4-methylenedioxyamphetamine to obtain L-Lys-(R,S)-MDA, and
    (B) alkylating an amide nitrogen of Boc-L-Lys(Boc)-3,4-methylenedioxyamphetamine to obtain Boc-L-Lys(Boc)-3,4-methylenedioxymethamphetamine, and deprotecting Boc-L-Lys(Boc)-3,4-methylenedioxymethamphetamine to obtain L-Lys-(R,S)-MDMA.

2. A method of synthesizing a pharmacological compound substance including the steps of:
    reducing 1-(3,4-Dibenzyloxyphenyl)-2-nitropropene to a ketone 3,4-Dibenzyloxyphenylacetone;
    applying reductive amination conditions to 3,4-Dibenzyloxyphenylacetone to obtain 3,4-Dibenzyloxymethamphetamine hydrochloride;
    reacting 3,4-Dibenzyloxymethamphetamine hydrochloride with an activated lysine derivative to obtain Boc-L-Lys(Boc)-3,4-dibenzyloxymethamphetamine;
    performing a hydrogenolytic removal of O-benzyl groups on Boc-L-Lys(Boc)-3,4-dibenzyloxymethamphetamine to obtain Boc-L-Lys(Boc)-3,4-dihydroxymethamphetamine;
    O,O'—methylating Boc-L-Lys(Boc)-3,4-dihydroxymethamphetamine to obtain Boc-L-Lys(Boc)-3,4-methylenedioxymethamphetamine; and
    deprotecting Boc-L-Lys(Boc)-3,4-methylenedioxymethamphetamine to obtain L-Lys-(R,S)-MDMA.

\* \* \* \* \*